(12) United States Patent
Baker et al.

(10) Patent No.: US 7,574,306 B1
(45) Date of Patent: Aug. 11, 2009

(54) METHOD AND SYSTEM FOR OPTIMIZATION OF POLYMER SEQUENCES TO PRODUCE POLYMERS WITH STABLE, 3-DIMENSIONAL CONFORMATIONS

(75) Inventors: David Baker, Seattle, WA (US); Brian Kuhlman, Chapel Hill, NC (US)

(73) Assignee: University of Washington, Seattle, WA (US)

( * ) Notice: Subject to any disclaimer, the term of this patent is extended or adjusted under 35 U.S.C. 154(b) by 371 days.

(21) Appl. No.: 11/043,907

(22) Filed: Jan. 26, 2005

Related U.S. Application Data

(63) Continuation-in-part of application No. 10/995,021, filed on Nov. 22, 2004, now abandoned.

(60) Provisional application No. 60/523,630, filed on Nov. 20, 2003.

(51) Int. Cl.
*G06F 19/00* (2006.01)
(52) U.S. Cl. ...................................................... 702/20
(58) Field of Classification Search .................... 702/20
See application file for complete search history.

(56) References Cited

U.S. PATENT DOCUMENTS 5,436,850 A * 7/1995 Eisenberg et al. ............. 703/11
2002/0106694 A1* 8/2002 Mayo et al. ................... 435/7.1

OTHER PUBLICATIONS

Dahiyat, Bassil I and Mayo, Stephen L., "DeNovo Protein Design: Fully Automated Sequence Selection," Science, vol. 278, Oct. 3, 1997, pp. 82-87.
Desjarlais, John R. and Handel, Tracy M., "Denovo design of the hydrophobic cores of proteins," Protein Science, 1995, pp. 2006-2018.
Ponder, Jay W., and Richard, Frederic M., "Tertiary Templates for Proteins," J. Mol. Biol., 1987, vol. 193, pp. 775-791.
Reina, Jose et al., "Computer-aided design of a PDZ domain to recognize new target sequences," Nature Pub. Group, Jun. 24, 2002.
Looger, Loren L., et al., "Computational design of receptor and sensor proteins with novel functions," Nature Pub. Group, 2003, pp. 185-190.
Malakauskas, Sandra M. and Mayo, Stephen L., "Design, structure and stability of a hyperthermophilic protein variant," Nature Pub. Group, Jun. 1998, vol. 5, No. 6, pp. 470-475.
Johnson, Eric C., et al., "Solution structure and dynamics of a designed hydrophobic core variant of ubiquitin," ScienceDirect, Aug. 1999, vol. u, Issue 8, pp. 967-968.
Koehl, Patrice and Levitt, Michael, "Denovo protein design.I. in search of stability and specificity," Jor. of Mol. Biology, Nov. 1999, vol. 293, Issue 5.
Kuhlman, Brian and Baker, David, "Native protein sequences are close to optimal for their structures," PNAS, Sep. 12, 2000, vol. 97, No. 19.
Jaramillo, Alfonso et al., "Folding free energy function selects mative-like protein sequences in the core but not on the surface," PNAS, Oct. 15, 2002, vol. 99, No. 21.
Raha, Kaushik et al., "Prediction of amino acid sequence from structure," Protein Science, 2000, pp. 1106-1119.
Su, Alyce and Mayo, Stephen L., "Coupling backbone flexibility and amino acid sequence selection in protein design," Protein Science, 1997, pp. 1701-1707.
Larson, Stefan M. et al., "Throughly sampling sequence space: Large-scale protein design of structural ensembles," Protein Science, 2002, pp. 2804-2813.
Harbury, Pehr B., et al., "High-Resolution Protein Design with Backbone Freedom," Science, Nov. 20, 1998, vol. 282, pp. 1462-1467.
Keating, Amy E., et al., "Side-chain repacking calculations for predicting structures and stabilities of heterodimetic coiled coils," PNAS, Dec. 18, 2001, pp. 14825-14830.
Bowers, Peter M., et al., "De novo protein structure determination using sparse NMR data," Jor. of Biomolecular, 2000, vol. 18, pp. 311-318.
Kortemme, Tanja et al., An Orientation-dependent Hydrogen Bonding Potential Improves Prediction of Specificity and Structure for Proteins and Protein-Protein Complexes, 2003.
Lazaridis, Themis and Karplus, Martin, "Effective Energy Function for PRoteins in Solution," PROTEINS, 1999, vol. 35, pp. 133-152.
Dunbrack, Roland, L., Jr., et al., "Bayesian statistical analysis of protein side-chain rotamer preferences," Protein Science, 1997, pp. 1661-1681.
Bonneau,Richard, et al. "Rosetta in CASP4: Progress in AB Initio Protein Structure Prediction," Proteins, 2001, pp. 119-126.

(Continued)

*Primary Examiner*—Jerry Lin
(74) *Attorney, Agent, or Firm*—Olympic Patent Works PLLC

(57) ABSTRACT

One embodiment of the present invention is directed to a method and system for designing the monomer sequence of a polymer to produce a particular polymer that adopts an initially specified, 3-dimensional conformation in a specified chemical environment. In one specific embodiment, the method and system produces amino-acid sequences for polypeptides in order to generate polypeptides that adopt initially specified, 3-dimensional conformations. Additional embodiments determine sequences for various other types of biopolymers in order to produce biopolymers that adopt specific conformations in specified chemical environments. For example, these method embodiments may be used to design sequences for polysaccharides, polynucleotides, and hybrid biopolymers.

20 Claims, 31 Drawing Sheets

OTHER PUBLICATIONS

Altschul, Stephen F., et al., "Gapped BLAST and PSI-BLAST: a new generation of protein database search programs," Nucleic Acids Research, 1997, vol. 25, No. 17, pp. 3389-3402.

Myers, Jeffrey K., et al., "Denaturant m values and heat capacity changes: Relation to changes in accessible surface areas of protein unfolding," Protein Science, 1995.

Plaxco, Kevin W., et al., "Contact order, transition state placement and the refolding rates of single domain proteins," Jor. of Mol. Bio., Apr. 10, 1998.

Holm, Liisa, and Sander, Chris, "Dali: a network tool for protein structure comparison," Sciencedirect.com, Nov. 1995, vol. 20, Issue 11, pp. 478-480.

Havranek, James J. and Harbury, Pehr B., "Automated design of specificity in molecular recognition," Nature Pub. Group, Dec. 2, 2002.

Mirny, Leonid and Shakhnovich, Eugene, "Evolutionary conservation of the folding nucleus," Jor. of Mol. Bio., Apr. 27, 2001, vol. 308, Issue 2.

Abeygunawardana, Mori S., et al., Improved Sensitivity of HSQS Spectra of Exchanging Protons at Short Interscan Delays using a New Fast HSQC (FHSQC).

Dectection Scheme Taht Avoids Water Saturation, Jul. 1995, vol. 108, Issue 1.

* cited by examiner

| component | cost |
|---|---|
| 102 — α | 8 |
| 104 — β | 14 |
| 106 — γ | 4 |

Figure 1

| pair | cost | pair | cost |
|---|---|---|---|
| 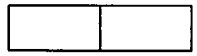 | 2 | 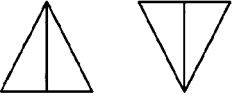 | 2 |
| 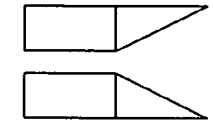 | 1 |  | 2 |
|  | 4 | 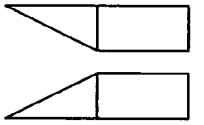 | 1 |
|  | 4 | 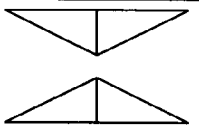 | 1 |
| 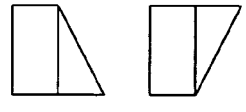 | 3 | 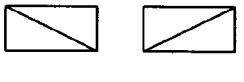 | 2 |
| 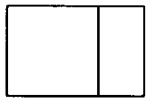 | 4 | 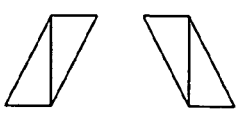 | 2 |
|  | 4 | 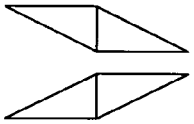 | 1 |
|  | 3 | | |
|  | 3 | | |
|  | 3 | | |
Figure 2

SEQUENCE LISTING

<160> NUMBER OF SEQ ID NOS: 1

<210> SEQ ID NO 1
<211> LENGTH: 93
<212> TYPE: PRT
<213> ORGANISM: Artificial
<220> FEATURE:
<223> OTHER INFORMATION: Synthetic polypeptide

<400> SEQUENCE: 1

Asp Ile Gln Val Gln Val Asn Ile Asp Asp Asn Gly Lys Asn Phe Asp
1               5                   10                  15

Tyr Thr Tyr Thr Val Thr Thr Glu Ser Glu Leu Gln Lys Val Leu Asn
            20                  25                  30

Glu Leu Lys Asp Tyr Ile Lys Lys Gln Gly Ala Lys Arg Val Arg Ile
        35                  40                  45

Ser Ile Thr Ala Arg Thr Lys Lys Glu Ala Glu Lys Phe Ala Ala Ile
    50                  55                  60

Leu Ile Lys Val Phe Ala Glu Leu Gly Tyr Asn Asp Ile Asn Val Thr
65                  70                  75                  80

```
                            -continued
Phe Asp Gly Asp Thr Val Thr Val Glu Gly Gln Leu Glu
                85                  90
```

US 7,574,306 B1

METHOD AND SYSTEM FOR OPTIMIZATION OF POLYMER SEQUENCES TO PRODUCE POLYMERS WITH STABLE, 3-DIMENSIONAL CONFORMATIONS

CROSS-REFERENCE TO RELATED APPLICATION

This application is a continuation-in-part of U.S. application Ser. No. 10/995,021, filed Nov. 22, 2004, now abandoned which claims the benefit of Provisional Application No. 60/523,630, filed Nov. 20, 2003.

STATEMENT OF GOVERNMENT LICENSE RIGHTS

The U.S. Government has a paid-up license in this invention and the right in limited circumstances to require the patent owner to license others on reasonable terms as provided for by the terms of Grant No. 5R01 GM051888-07 awarded by the National Institute of Health.

COMPUTER PROGRAM LISTING APPENDIX

Two identical CDs identified as "Disk 1 of 2" and "Disk 2 of 2," containing program source code implementing an embodiment of the present invention, are included as a computer program listing appendix. The program text can be viewed on a personal computer running a Microsoft Windows operating system, using Microsoft Notepad or other utilities used for viewing ASCII files. Each disk contains the following directories and files:

Design_structure.txt
Pack.txt

SEQUENCE PROGRAM LISTING APPENDIX

Two identical CDs identified as "Copy 1 of 2" and "Copy 2 of 2," containing the sequence listing for the present invention, is included as a sequence listing appendix.

TECHNICAL FIELD

The present invention is related to optimization in high dimensional problem domains, including the design of polymer sequences in order to produce polymers with initially specified, stable, 3-dimensional configurations and, in particular, to a method and system for designing amino-acid sequences of polypeptides in order to produce polypeptide molecules with initially specified, stable, 3-dimensional conformations.

BACKGROUND OF THE INVENTION

Over the past 100 years, intensive research efforts have been directed to elucidating and understanding the structures and functions of biopolymers, and biopolymer structure determination and structural information continue to play a key role in many major scientific areas, including biochemistry, molecular biology, biophysics, genomics, proteomics, and structural biology. Rapid progress has been made in developing powerful and refined tools, including x-ray crystallography and nuclear magnetic resonance, to rapidly determine the atomic-level structure of small molecules and of many classes of biopolymers, including globular proteins that perform critical catalytic, signaling, and transport functions within living cells. As a greater number of 3-dimensional globular protein structures have become available, structural biologists have begun to determine many of the principals that determine, and structural motifs common to, globular protein conformations in various chemical environments, including aqueous solutions, concentrated, complex solutions found in cells, and environments within protein crystals.

Because not all known proteins are amenable to structure determination by currently available technologies, and because enormous amounts of protein-sequence data are becoming available through the rapid determination of genome sequences, a large effort is underway to develop methods for accurately predicting 3-dimensional protein structures based on the amino-acid sequence of proteins. Although progress has been made, methods for accurately predicting 3-dimensional protein structure over a wide variety of protein types and sizes have not yet been developed. More recently, efforts have been undertaken to develop computational methods for designing the amino-acid sequences of artificial proteins, and for modifying the amino-acid sequences of naturally occurring proteins, in order to produce artificial protein molecules and modified naturally occurring protein molecules with initially specified 3-dimensional conformations. There are many uses for such methods. A number of uses involve designing and testing small sequences in order to further elucidate the structural motifs of, and sequence-dependent effects on, naturally occurring 3-dimensional protein structures. The ability to design proteins with specific 3-dimensional conformations may also facilitate elucidation of various aspects of enzyme catalysis, allosteric regulation of enzymes, and various types of conformation-related associations between proteins and between proteins and other types of biopolymers. Methods for designing sequences to produce specified, stable 3-dimensional protein conformations may also find wide applicability in the development of protein catalysts and signaling and binding molecules that may find use in diagnostics, therapeutics, nanotechnology, and other areas related to medicine, molecular electronics, and materials science.

While, in general, the amino-acid sequence of a globular protein determines the stable conformation or conformations of the protein in aqueous solution and in the complex environments of living cells, it is a computationally difficult problem to predict those stable conformations from the amino-acid sequence alone. One brute force approach is to evaluate every possible 3-dimensional conformation for a polypeptide having a particular amino-acid sequence, compute the free energy for each possible 3-dimensional conformation, and select, as the predicted 3-dimensional conformation or conformations, one or several of the lowest free-energy conformations. Unfortunately, the conformation state space is enormous. Even for relatively small polypeptides, there are far more possible conformations than there are elementary particles in the known universe. A trial-and-error method for designing a protein with a specific, target 3-dimensional conformation, in which the 3-dimensional conformations of a large number of polypeptides with different amino-acid sequences are predicted, and then compared to the target 3-dimensional conformation, involves searching a sequence/conformation state space of far greater size than that of a conformation state space. There are, for example, $20^n$ different possible amino-acid sequences for a polypeptide composed of a linear sequence of length n amino acids of some or all of the 20 commonly encountered amino acids. For this reason, a directed, constrained search for polypeptides of specific amino-acid sequences that adopt specified 3-dimensional conformations is needed. Current methods for predicting conformation changes resulting from amino acid substitutions in naturally occurring proteins with determined 3-dimensional structures is an example of a highly constrained search.

The problem of polypeptide sequence design to produce an initially specified, 3-dimensional conformation falls into the larger class of problems that involve mathematical optimization of multi-variable functions, and, in particular, mathematical optimization in high dimensional problem domains. Computer scientists and mathematicians seek general optimization techniques for determining optimal solutions for systems described by functions with large numbers of variables, and research scientists and technologists continue to seek methods for addressing the problem of designing amino-acid sequences in order to produce polypeptides that adopt specified, desired 3-dimensional conformations in solution.

SUMMARY OF THE INVENTION

One embodiment of the present invention is directed to a method and system for designing the monomer sequence of a polymer to produce a particular polymer that adopts an initially specified, 3-dimensional conformation in a specified chemical environment. In one specific embodiment, the method and system produces amino-acid sequences for polypeptides in order to generate polypeptides that adopt initially specified, 3-dimensional conformations in aqueous solution. Additional embodiments determine sequences for various other types of biopolymers in order to produce biopolymers that adopt specific conformations in specified chemical environments. For example, these method embodiments may be used to design sequences for polysaccharides, polynucleotides, and hybrid biopolymers.

BRIEF DESCRIPTION OF THE DRAWINGS

FIG. 1 shows a table that describes three different types of planer, 2-dimensional components.

FIG. 2 shows a table that indicates the cost for each type of pair-wise component attachment.

DETAILED DESCRIPTION OF THE INVENTION

Embodiments of the present invention are directed, in general, to finding near-global optima in high-dimension variable spaces, and specific embodiments are directed to designing polymer sequences in order to produce polymers that adopt specified 3-dimensional conformations in specified chemical environments. The present invention is discussed, below, in three subsections. The first subsection provides an overview of the optimization method used in the present invention, and illustrates the optimization method in the context of a relatively simple, graphically presented problem domain. In the next subsection, a detailed discussion of one embodiment of the present invention, an implementation of a method for designing amino-acid sequences to produce polypeptides with specified 3-dimensional conformations, is provided, with reference to control-flow diagrams. In a third subsection, polypeptides designed by the polypeptide-sequence design method discussed in the second subsection are described, with reference to illustrations of the initial 3-dimensional conformation specification and constraints and illustrations of the actual 3-dimensional conformation of a designed polypeptide determined by x-ray crystallography. FORTRAN code for the polypeptide-sequence-design method discussed in the second subsection is included as Appendix I to the current application. A sequence listing for the top7 polypeptide is provided in Appendix II. A list of related studies and methods is provided in Appendix III.

Figure 1:
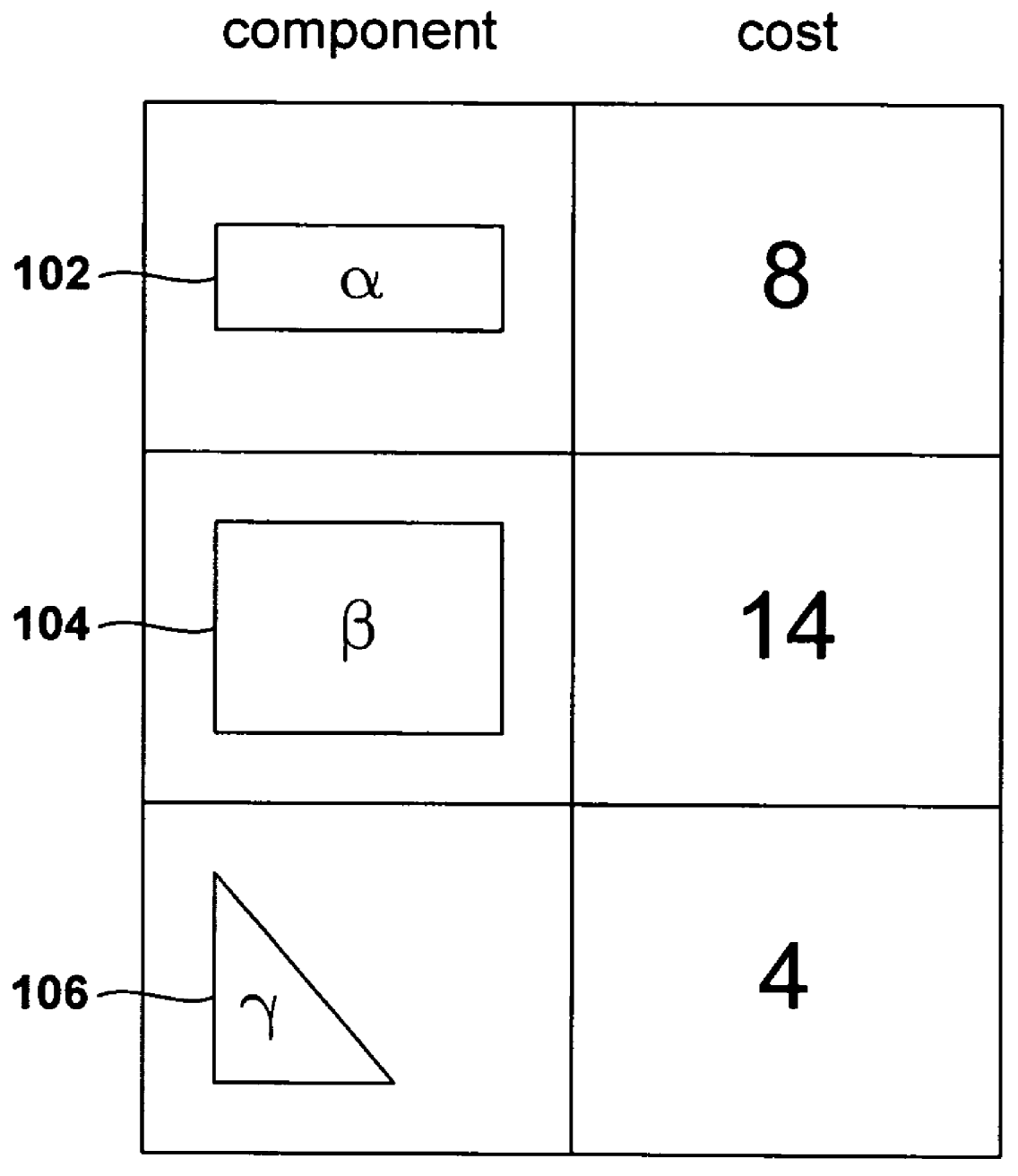

Overview of the Optimization Method Used in One Embodiment of the Present Invention The optimization method used in one embodiment of the present invention is described in the context of a relatively simple, abstract, 2-dimensional optimization problem. This problem involves the sequential attachment of three different kinds of planer components to form a component string with a linear component sequence having a particular 2-dimensional conformation. FIG. 1 shows a table that describes three different types of planer, 2-dimensional components. The table in FIG. 1 lists the three different types of planer components, along with a cost for including each of the different types of components in a component string. The components include: (1) a rectangular α component 102, with a cost of 8; (2) a square β component 104, with a cost of 14; and (3) a triangular γ component 1106, with a cost of 4.

In addition to a per component cost for including a particular type of component in a component string, there is a cost for each type of pair-wise attachment of components used to form a linear sequence of components in a component string. FIG. 2 shows a table that indicates the cost for each type of pair-wise component attachment.

Figure 3A:
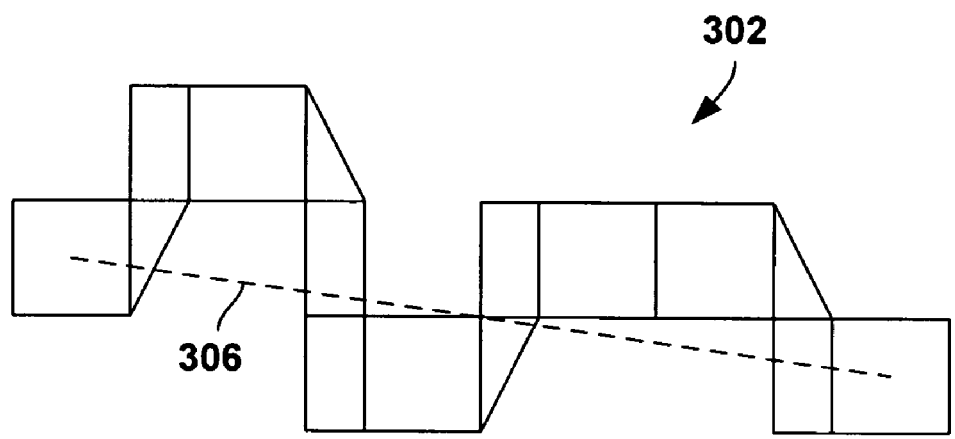
FIGS. 3A-B illustrate two different possible conformations of a component string.
Figure 3B:
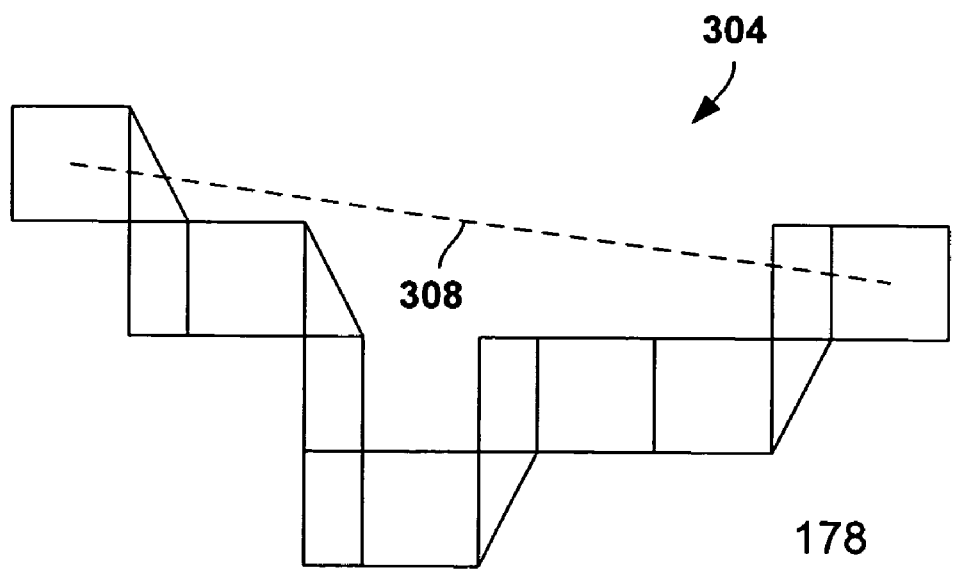

FIGS. 3A-B illustrate two different possible conformations of a component string. The two conformations shown in FIGS. 3A-B 302 and 304 are only two of many different possible 2-dimensional structures, or conformations, that can be formed by the sequence of components βγαβγααβγαβ-βγαβ. The total cost for each of the two conformations is obtained by adding together the per component costs of the individual components, as shown in FIG. 1, and the pair-wise attachment costs, as shown in FIG. 2, for the components in the two conformations. Both conformations have, in the case illustrated in FIGS. 3A-B, a total cost of 178.

To form a component string, each interior component is attached to a preceding component and to a succeeding component along two edges, according to the possible attachment types shown in FIG. 2, with the starting and ending components of he component string attached only to a succeeding and a preceding component, respectively, along a single edge. Component strings can thus be described as linear component-type sequences. Components cannot overlap one another. There are three different possible conformations for each non-ending component. A succeeding component can be attached along any of three free edges for each of the α and β components, and a succeeding component can be attached along either of two free edges for a γ component, which, lacking two-fold symmetry, can have two different orientations.

It is easily observed that the overall 2-dimensional structure, or conformation, of the two 15-component component strings in FIGS. 3A-B is different. The first conformation 302 first rises, and then descends, in a vertical direction as the component string is traversed from left to right, while the second conformation 304 descends, and then rises. The distances 306 and 308 and directions between the starting and ending points of the two different conformations, however, are identical. Thus, component substrings equivalent to the two component strings of FIGS. 3A-B can be substituted for one another within a larger component string without changing the global conformation of the larger component string other than the local change related to the different conformations of the substrings, provided that neither of the conformations overlie, or interfere with, other parts of the larger component string.

Figure 4A:
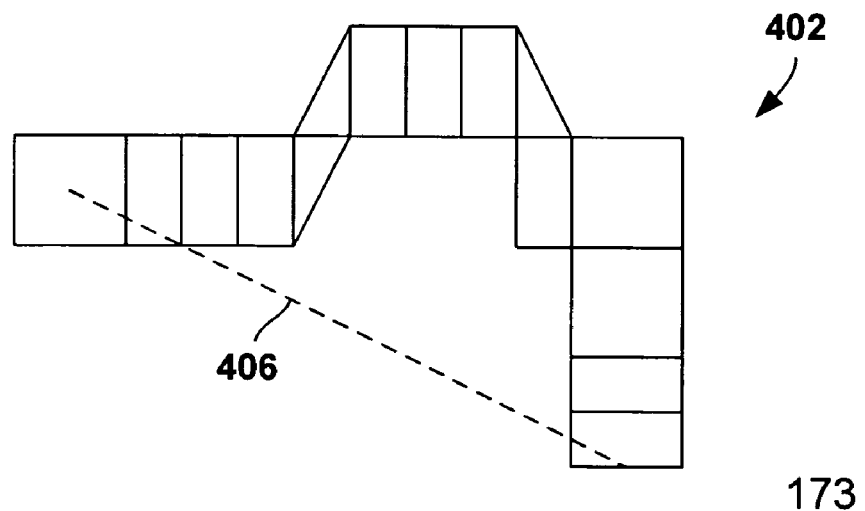
FIGS. 4A-B illustrate two different 15-component component strings, with two different sequences, having the same conformation.
Figure 4B:
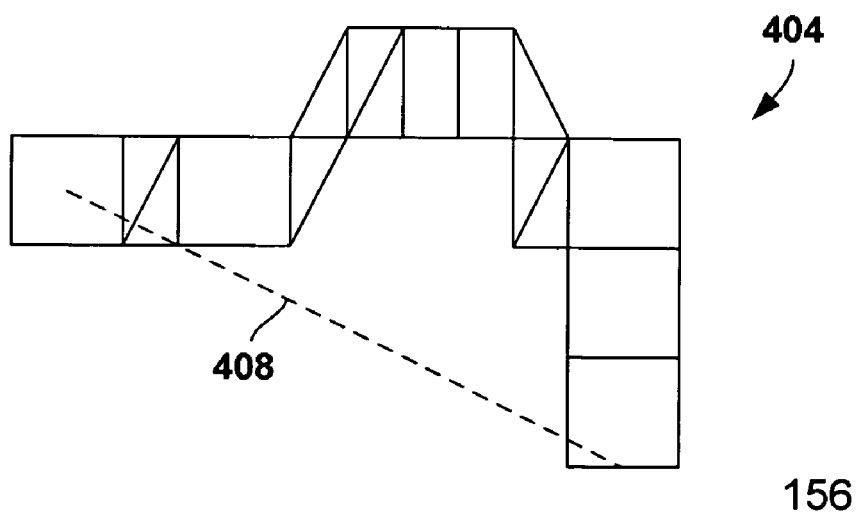

FIGS. 4A-B illustrate two different 15-component component strings, with two different sequences, having the same conformation. The sequence of the component string 402 shown in FIG. 4A has the component sequence βαααγγαα-αγαββαα, while the component string 404 shown in FIG. 4B has the sequence βγγβγγγγβγγγββββ. The total cost for the first component string 402 is 173, while the total cost for the second component string 404 is 156. Both of the component strings shown in FIGS. 4A-B have the same length, in components, and identical distances and directions between starting and ending points, 406 and 408. As for the two conformations of the component string shown in FIGS. 3A-B, the two different component strings shown in FIGS. 4A-B could be interchanged, as substrings within a larger component string, without affecting the global conformation of the larger string.

FIGS. 3A-B and 4A-B illustrate that, given a fixed starting point and ending point in 2-dimensional space, many different alternative component strings with different sequences and conformations may be constructed that begin at the specified starting point and end at the specific ending point. The different, alternative component strings that can be constructed to conform to a starting-point/ending-point constraint may differ in length, in sequence, in conformation, or in any combination of length, sequence, and conformation. In general, a particular component-string conformation is determined both by the component sequence of the component string and the conformations of the individual components within the component string. Even for a relatively simple problem domain related to constructing different component strings from the three component types shown in the table of FIG. 1, a component string of length 20 can have $3^{20}$, or nearly 3.5 billion, possible sequences when component strings are considered to be ordered, or, in other words, to have starting and ending points. The number of conformations of a given component string with a given component sequence of length 20 may approach $3^{20}$, depending on the number of conformations disallowed for component overlap.

When the state space of different possible sequence/conformation pairs of a component string of a particular length n is considered, the state space can be considered to have 2n dimensions, consisting of n component-type dimensions corresponding to the type of component at each position within the component string and n conformation dimensions corresponding to the component conformation at each of the n different positions within the component string. Thus, the sequence/conformation state space for the simple system of component strings has 40 nearly independent, orthogonal dimensions and is populated by a number of different sequence/conformation pairs approaching $3^{2n} \approx 10^{38}$, a number nearly as large as one half of the total number of elementary particles in the universe. The conformation dimensions are not entirely independent, and the number of possible sequence/conformation pairs less than $3^{2n}$, because component overlap is not allowed.

Figure 5:
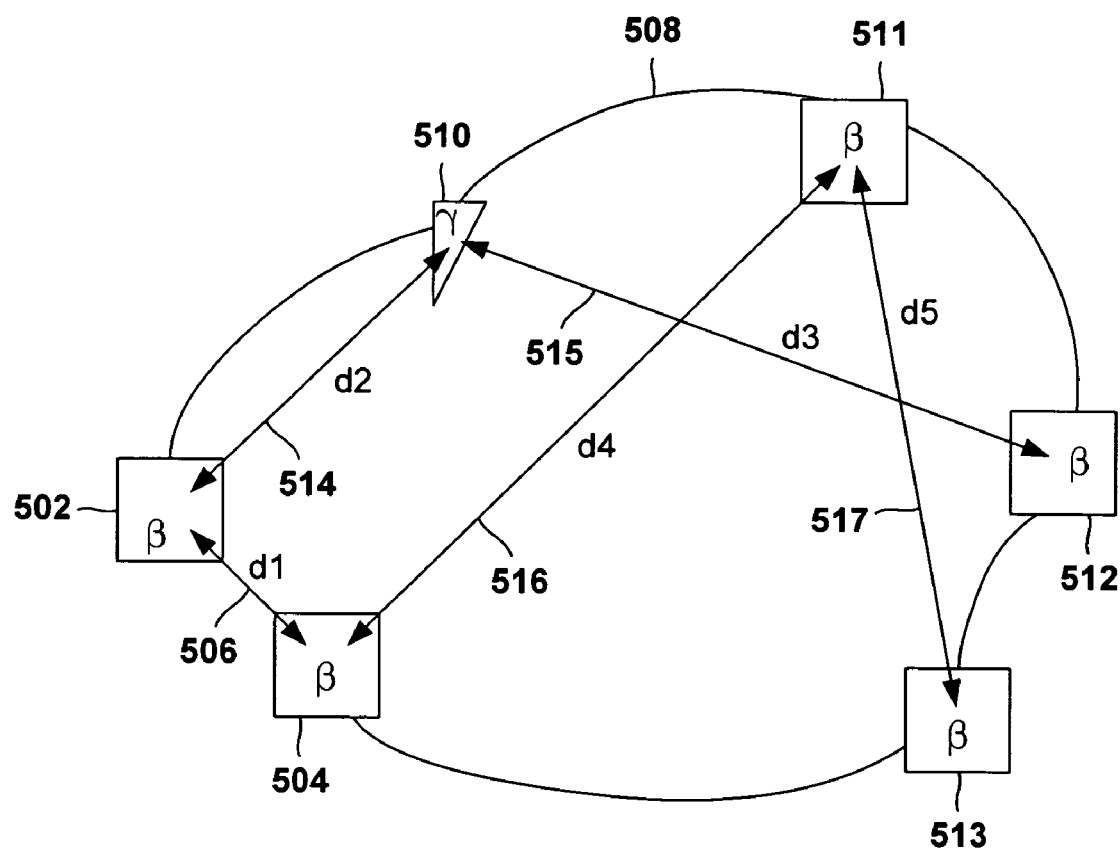
FIG. 5 illustrates an example of a specific optimization problem in the context of the 2n-dimensional sequence/conformation space of a component string of length n.

FIG. 5 illustrates an example of a specific optimization problem in the context of the 2n-dimensional sequence/conformation space of a component string of length n. In FIG. 5, a schematic representation of a desired 2-dimensional conformation for a component string, along with a set of constraints, is shown. The desired conformation has a starting point 502 and an ending point 504 separated by a specified distance $d_1$ 506. A rough approximation of a desired shape for the component string is given by the curved line 508. The constraints include component-type constraints. For example, the desired conformation has a β component 502 at the starting point, a β component 504 at the end, and a γ component 510 and three additional β components 510, 511, and 512 at specified locations along the component string. In addition, there are a number of additional distance constraints 514-517 between the various specified components within the component string. The optimization problem is to determine a component sequence that, with appropriate conformations for the components of the sequence, produces a component-string that satisfies the 2-dimensional conformation constraints specified in FIG. 5 that has the lowest possible total component-string cost. The optimization problem can be more concisely expressed as:

$$\frac{\min}{n, ctype_{k=1 \text{ to } n}, conformation_{k=1 \text{ to } n}} \left( \sum_{k=1}^{n} C_k + \sum_{k=1}^{n-1} P_{k,k+1} \right)$$

given the constraints of FIG. 5 where $C_k$ is the component-type cost of component k;

n is the length of the component string;

$P_{k,k+1}$ is the cost of attaching component k to component k+1; and the minimization is over all possible sequences and conformations.

Figure 6A:
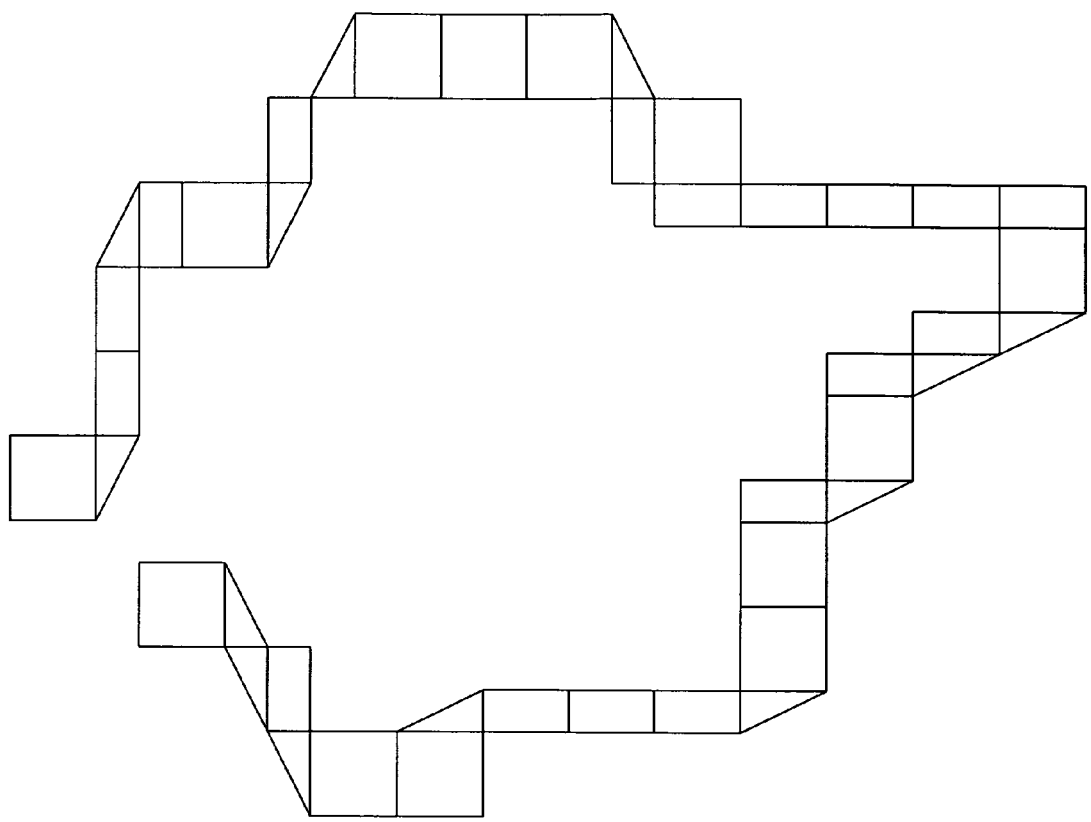
FIGS. 6A-B show two possible sequence/conformation pairs that meet the sequence and distance constraints of FIG. 5, and roughly conform to the shape indicated in FIG. 5.
Figure 6B:
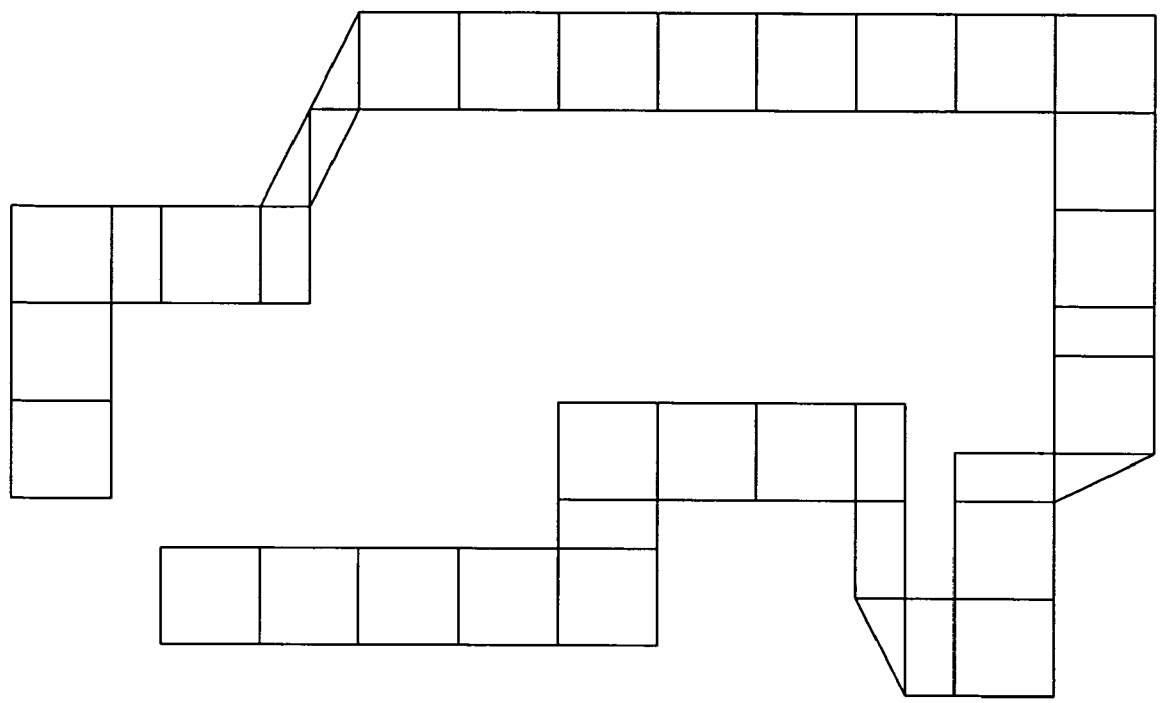

An additional constraint for the above problem is to fix n at some particular, reasonable value, or to a range of values. When n is not fixed, the conformational space that needs to be searched is infinitely dimensional. However, whether infinitely dimensional or finitely dimensional, at least locally minimal solutions for the optimization problem can be found by any of a number of well-known, high dimensional optimization methods. FIGS. 6A-B show two possible sequence/conformation pairs that meet the sequence and distance constraints of FIG. 5, and roughly conform to the shape indicated in FIG. 5. The optimization problem, if conducted by brute force, would evaluate every possible sequence/conformation pair, such as the two shown in FIGS. 6A-B, and choose as a solution the sequence/conformation pair having the lowest total cost.

Figure 7:
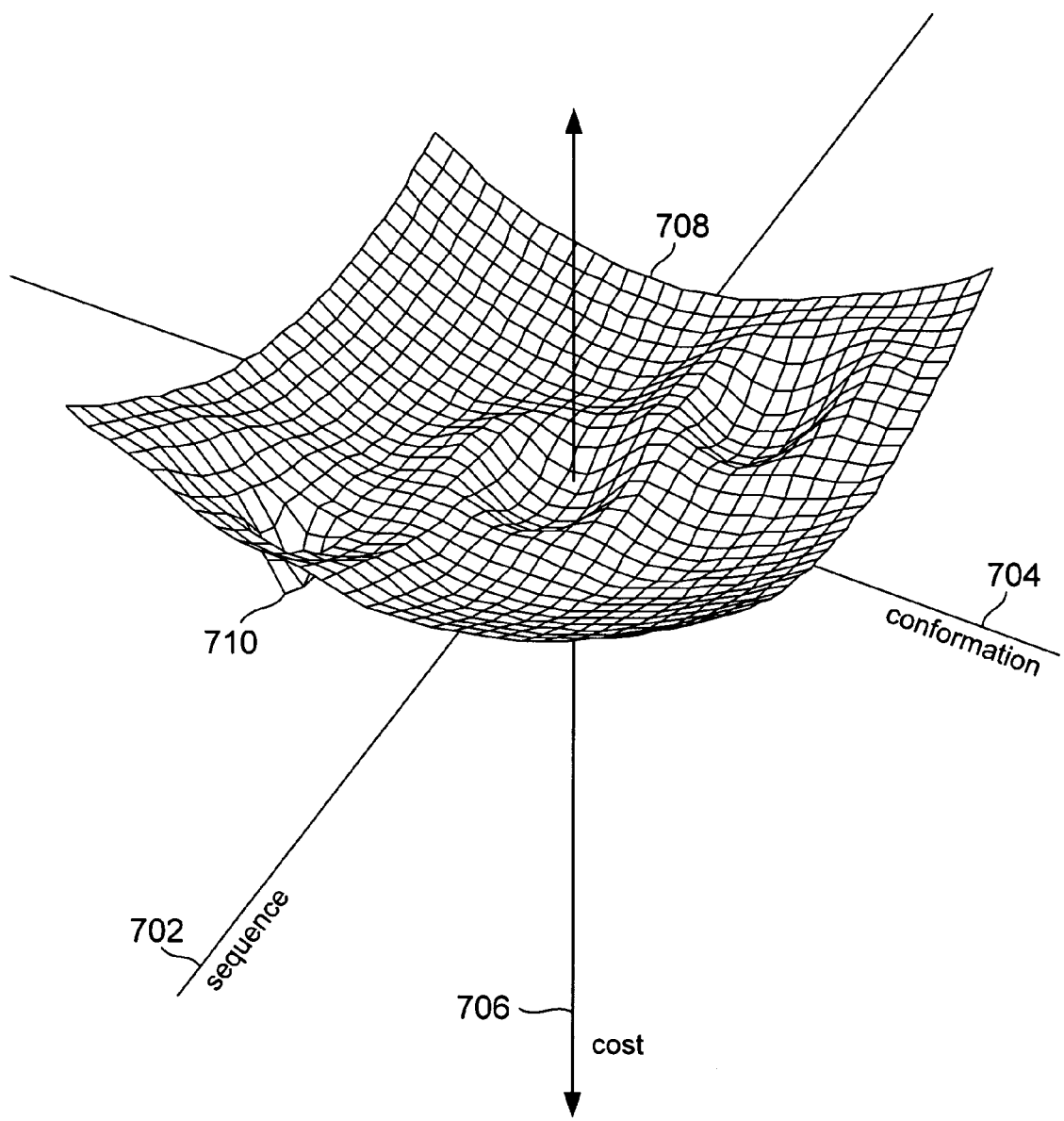
FIG. 7 shows a conceptual representation of the optimization problem discussed with reference to FIGS. 1 and 6.

FIG. 7 shows a conceptual representation of the optimization problem discussed with reference to FIGS. 1 and 6. As discussed above, the optimization problem concerns a 2n-dimensional component-string sequence/conformation state space, or problem domain. Graphical representation of state spaces of dimensions greater than three is notoriously difficult. Therefore, in order to provide graphical representations of the problem domain, as well as to conveniently set up the illustrations for describing one embodiment of the optimization method of the present invention, the 2n-dimensional sequence/conformation space is projected onto two dimensions in FIG. 7, a sequence dimension represented by a sequence access 702 and a conformation dimension represented by a conformation axis 704. Thus, the sequence axis 702 represents a single dimension onto which the n sequence dimensions are projected, and the conformation axis represents a single dimension onto which the n conformation dimensions are projected. The optimization problem is therefore a 3-dimensional problem, by the conventions adopted for FIG. 7, where the cost is a third dimension, represented by the cost axis 706. Thus, all possible sequence/conformation pairs are mapped to the sequence/conformation surface 708, a portion of which is shown in FIG. 7, where the height of a point on the sequence/conformation surface with respect to the cost axis represents the cost of the sequence/conformation pair represented by the point.

As can be seen in FIG. 7, there are a number of well-like depressions in the surface, including a rather deep well 710 that may represent a local minimum in the problem space, or a global minimum if, in fact, the cost value for the well 710 is lower than that for any other conformation in the sequence/conformation space represented by the surface 708. It should be noted that the hypothetical surface shown in FIG. 7 does not correspond to any particular region of the actual surface for the problem domain discussed with respect to FIGS. 5 and 6, but is instead employed in FIG. 7, and in figures that follow FIG. 7, for illustrating optimization methods. It is the case, however, that the surfaces for problems such as the problem discussed above with reference to FIGS. 5 and 6 generally include well-like local optima as well as longer-range hills and valleys that together form a complexly shaped surface, a given small portion of which may resemble the portion of the surface shown in FIG. 7.

Figure 8:
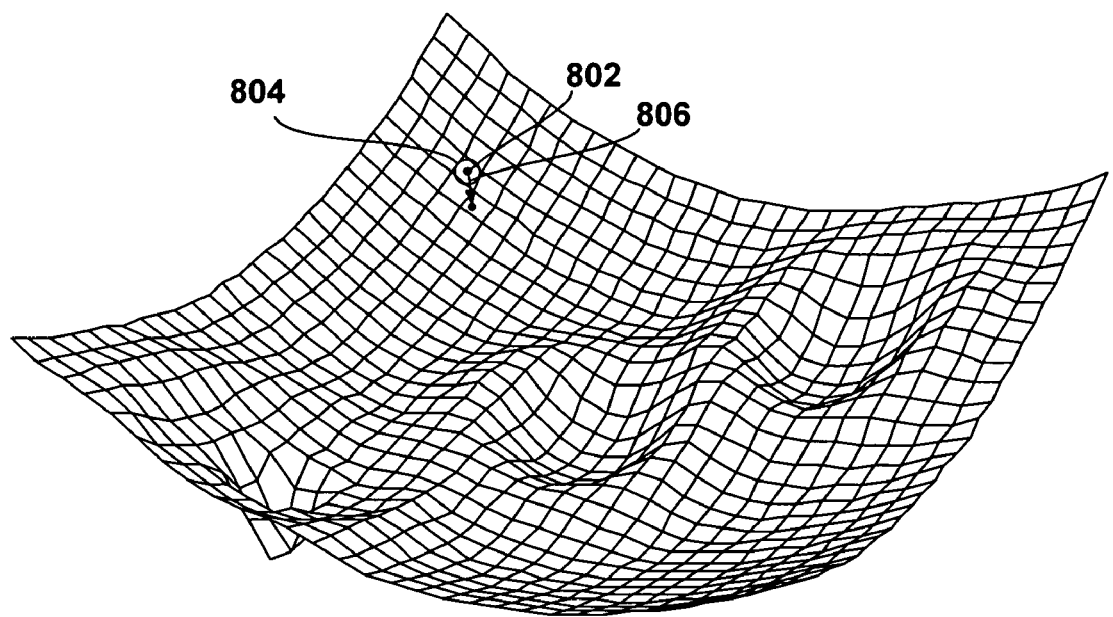
FIGS. 8-10 illustrate one standard approach to seeking an optimal component sequence with respect to defined constraints, such as for the problem posed with reference to FIG. 5.
Figure 9:
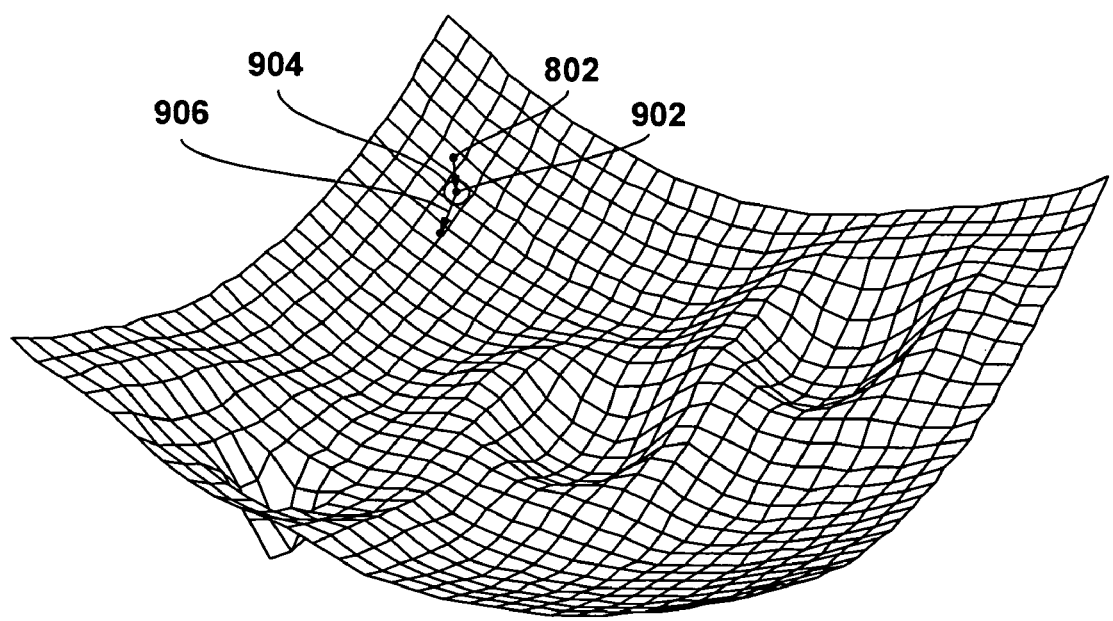
Figure 10:
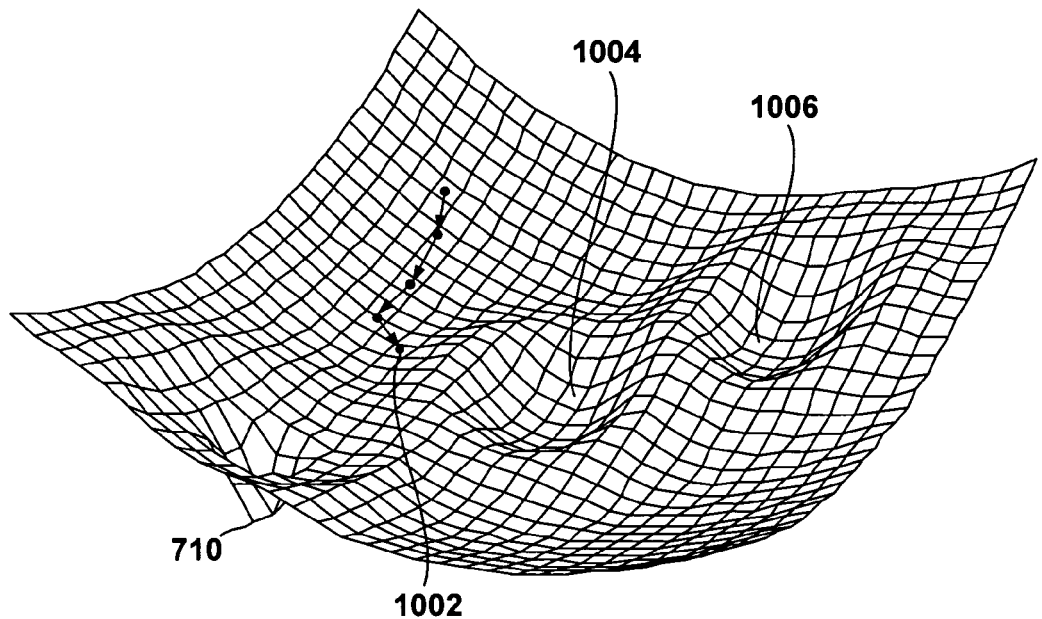

FIGS. 8-10 illustrate one standard approach to seeking an optimal component sequence with respect to defined constraints, such as for the problem posed with reference to FIG. 5. First, as shown in FIG. 8, a starting point 802 is selected. In general, the better the selected starting point, the more quickly a suitable local or near-global minimum can be found. However, in general, the problem of selecting a suitable starting point is of a computational order equivalent to the problem of finding a near-optimal solution for the original problem. Therefore, a normal approach for finding a suitable starting point is to employ empirical methods for selecting a reasonable starting point according to various empirical considerations, in the current case, a reasonable starting component sequence, such as the component sequence of the component string shown in FIG. 6B.

Next, a small region, or neighborhood 804, surrounding the starting point is analyzed in order to select a direction 806 in which to move along the surface, hopefully closer towards a local or near-global minimum. There are many methods for selecting a direction for a next move. One commonly employed method is the steepest-descent method, in which a gradient is computed for the starting point within the local neighborhood, and the direction 806 is the gradient vector pointing in the direction of lower cost. The gradient vector represents the direction of greatest cost reduction along the surface from the selected starting point. Next, as shown in FIG. 9, a new point 902 is selected in the gradient direction at some reasonably small distance from the starting point 802. Then, the neighborhood 904 surrounding the next point 902 is analyzed to determine a next gradient, or trajectory 906, along the surface that hopefully leads towards a local or near-global minimum. As shown in FIG. 10, this process is repeated multiple times until a local minimum 1002 is found. Note, however, that the local minimum 1002 shown in FIG. 10 as the end-point for a sequence/conformation state space search is not the potentially global minimum 710, nor either of the deeper local minima 1004 and 1006.

Figure 11:
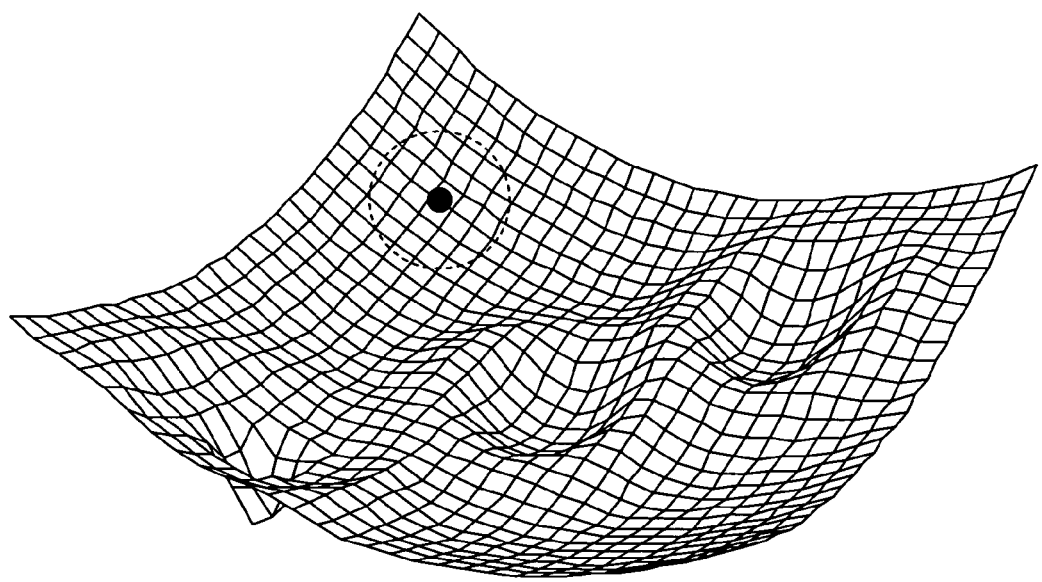
FIG. 11 shows an increase in the size of the neighborhood about the starting point shown in FIG. 8.

Considering the optimization method illustrated in FIGS. 8-10, one may wonder why, with the global and local minima so obviously prominent on the conformation surface, a more straightforward approach might not be taken. For example, one could simply the compute the cost for some well-distributed, large set of sequence/conformation pairs across the surface in order to quickly find the wells. Unfortunately, in high-dimensional problems, the number of states that would need to be searched to even extremely coarsely sample a large volume of the hyper-dimensional space would be far larger than a number of computations possible within any reasonable time period. Alternatively, one might wonder why the size of the neighborhood considered for the starting point and subsequent points along a trajectory towards a minimum might not be increased, in order to more accurately determine a direction for the search at each step. FIG. 11 shows an increase in the size of the neighborhood about the starting point shown in FIG. 8. However, in high-dimensional state spaces, an increase in neighborhood size, where the neighborhood size is a relative size of the number of states in a neighborhood with respect to the total number of states in the volume being searched, is also generally computationally intractable.

Figure 12A:
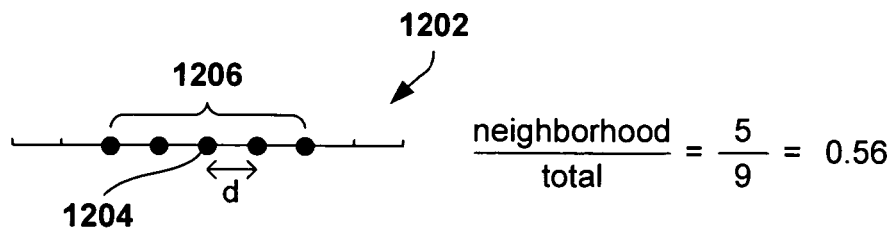
FIGS. 12A-C illustrate neighborhood-related problems in high-dimensional state spaces.
Figure 12B:
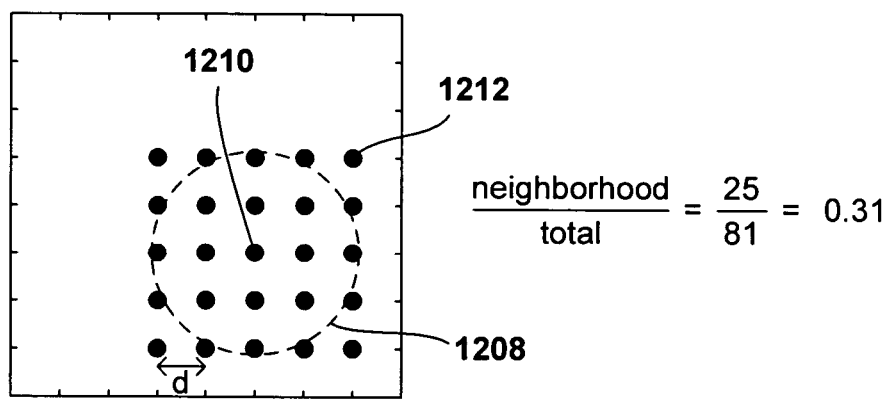
Figure 12C:
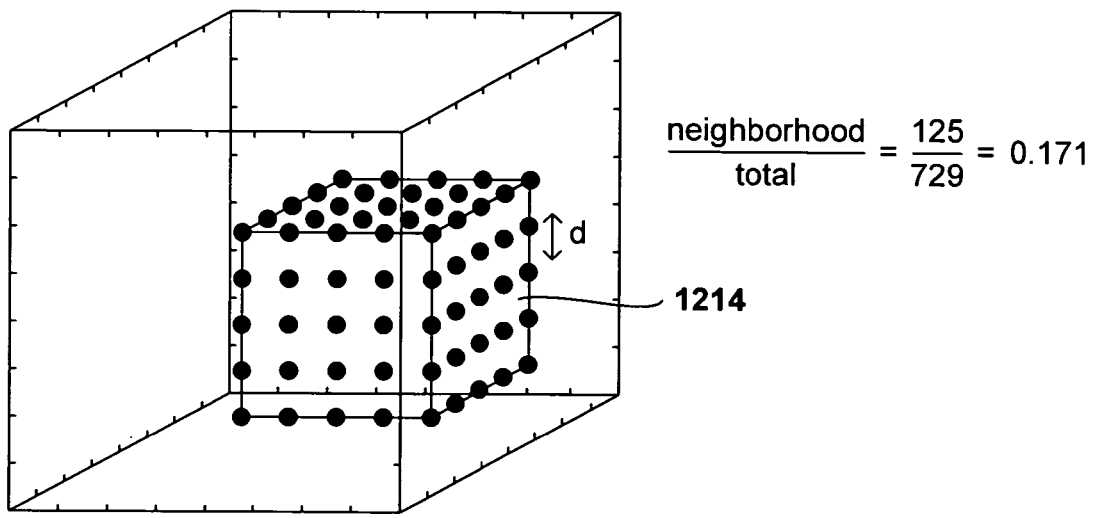

FIGS. 12A-C illustrate neighborhood-related problems in high-dimensional state spaces. In FIG. 12A, a 1-dimensional state space is shown 1202 that includes nine discrete states, represented by evenly spaced small and large disks. A central, starting-point state 1204 is centered within a neighborhood of states 1206 located within a distance of 2d from the starting point, with d being the inter-state spacing interval for the example. As shown in FIG. 12A, the 2d neighborhood therefore includes 0.56N, where N is the total number of states in the sample space. FIG. 12B shows a 2-dimensional state space, with nine states along each of two dimensions. FIG. 12B shows a disk-like 2d neighborhood 1208 about a selected sample point 1210. A square approximation for the neighborhood includes all the sample points, such as sample point 1212, in a square, planer region in which the disk-like 2d neighborhood is inscribed. In the 2-dimension case, the 2d neighborhood includes only 0.31N, where N=81. Similarly extending the example to three dimensions, as shown in FIG. 12C, the cube-like 2d neighborhood 1214 about a selected sample point (not shown in FIG. 12) includes only 0.171N, where N is 729. As can be seen in FIGS. 12A-C, as the dimensionality of a problem increases, despite a constant number of sample points in each dimension, the total number of sample points N increases exponentially with the number of dimensions, and the percentage of the number of sample points in a fixed-d neighborhood with respect to N decreases exponentially. In the relatively high-dimension problem domain discussed with reference to FIGS. 5 and 6, a method of optimization for which is discussed with reference to FIGS. 7-10, the neighborhood 804 considered for a particular point along a trajectory toward a local minimum needs to be quite small in order to encompass a computationally tractable number of sample points.

Figure 13:
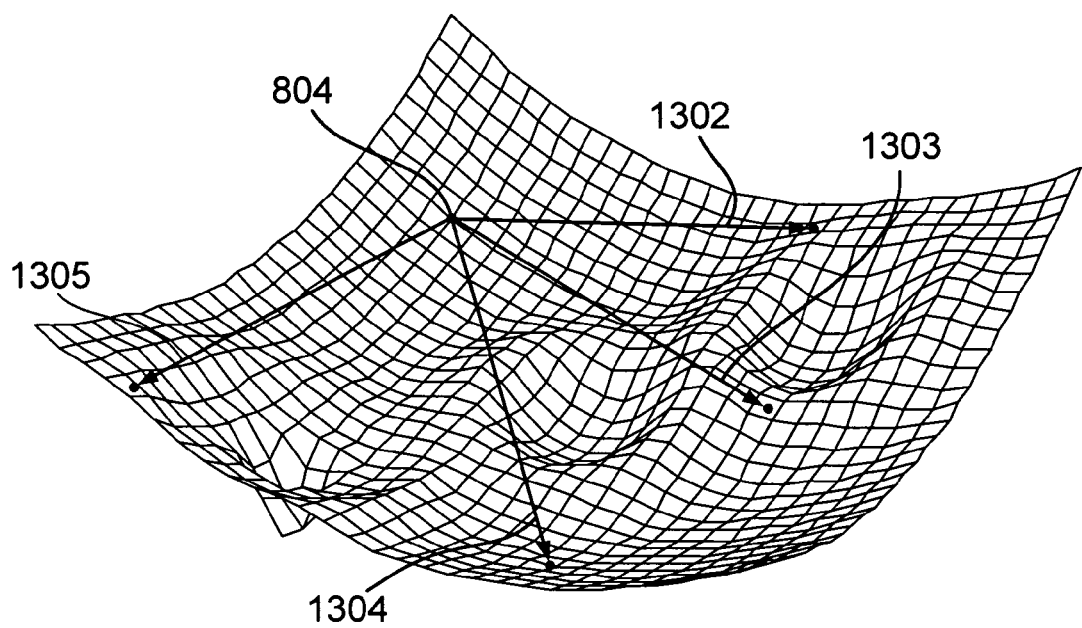
FIG. 13 illustrates a problem encountered with increasing the lengths of individual steps in a state-space search.

One might also wonder why, once a trajectory is computed based on the neighborhood of a particular sample point, a step of greater length might not be taken in order to more quickly traverse a path towards a local minimum. FIG. 13 illustrates a problem encountered with increasing the lengths of individual steps in a state-space search. In FIG. 13, relatively large magnitude steps 1302-1305 are taken in various directions from the starting point 804 used initially in FIG. 8. As can be seen in FIG. 13, the result of large steps is that the search path may end up passing over the wells in the surface, resulting in a search path that may completely miss many potential local and near-global minima, and result in unproductive, non-convergent oscillation about the surface.

Figure 14:
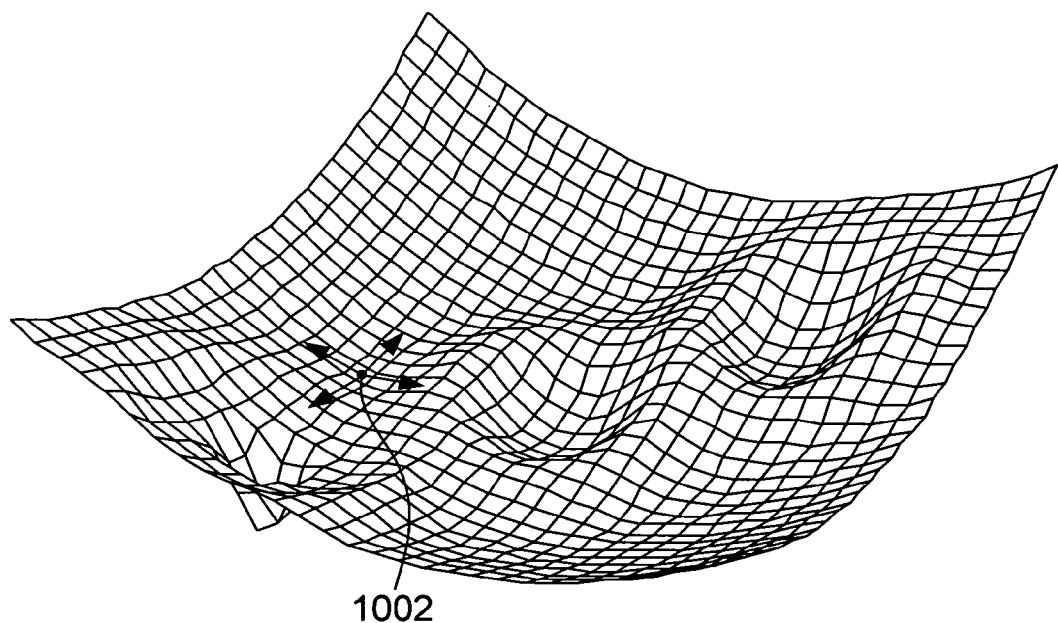
FIG. 14 shows a local minimum reached by the optimization method illustrated in FIG. 10.

Finally, in the complex problem domains normally encountered in high-dimensional state-space problems, many local minima are generally encountered, each representing a kind of local-minimum hazard with respect to effective searching. FIG. 14 shows a local minimum reached by the optimization method illustrated in FIG. 10. FIG. 14 shows the local minimum 1002 reached by the optimization method illustrated in FIG. 10. At this local minimum point, a path in any direction along the surface leading away from the local minimum initially results in increasing cost, or, in other words, in a path with a positive component along the cost axis. Therefore, an optimization method that relies purely on a steepest-descent vector computed from a local neighborhood terminates at a local minimum, such as the local minimum 1002 in FIG. 14, despite the fact that much lower-cost local minima are close by on the sequence/conformation surface. As the dimensionality of the problem domain increases, the above-discussed problems with traditional optimization methods increase exponentially. The huge number of states within the state-space volume of a high-dimensional problem and the generally large number of local minima prevents computationally effective searching by purely steepest-descent methods, such as the method described above with respect to FIGS. 7-10.

Figure 15:
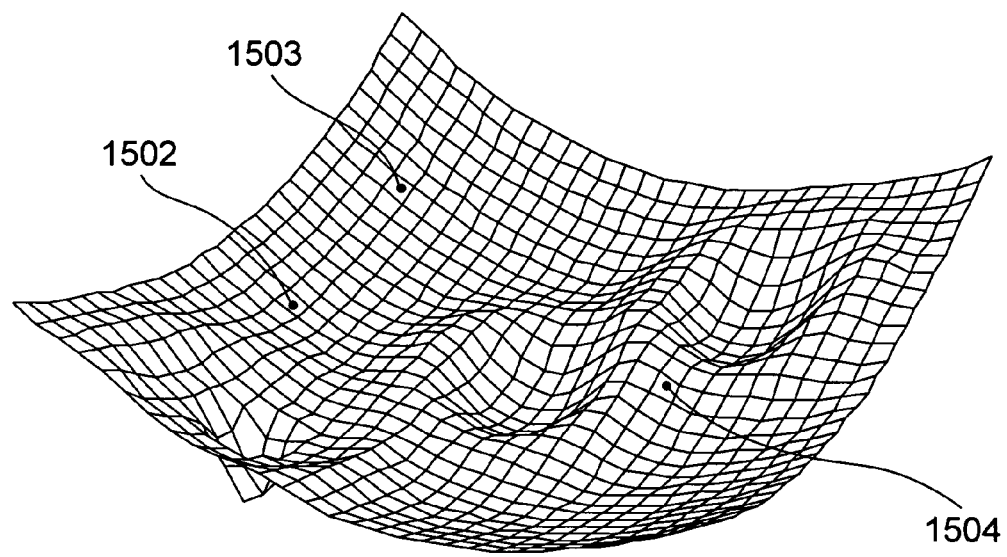
FIGS. 15-18 illustrate a general optimization method for high dimensional problem domains that represents one embodiment of the present invention.
Figure 16:
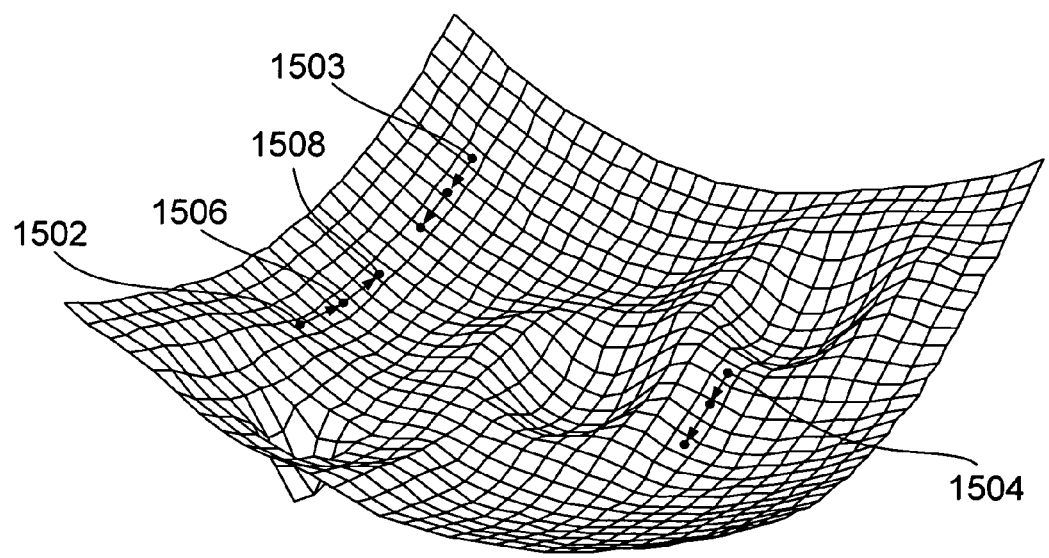

FIGS. 15-18 illustrate a general optimization method for high dimensional problem domains that represents one embodiment of the present invention. This method employs several different strategies to reducing the number of computations necessary in order to search a high-dimensional state space for near-global minima. First, as shown in FIG. 15, the method employs multiple starting points 1502-1504, rather than a single starting point (e.g. starting point 804 in FIG. 8). By using multiple starting points, multiple separate paths, or threads, can be concurrently or simultaneously followed along the state-space surface in order to seek out different local minima. Moreover, as shown in FIG. 16, a number of separate threads are launched from each of the multiple starting points 1502-1504. In FIG. 16, two different secondary points, such as points 1506 and 1508, are computed for each starting point. Each of these secondary points serves as a starting point for a separate thread, or path. The threads may be concurrently, simultaneously, or both concurrently and simultaneously followed towards local minima. Multi-tasking approaches allow for concurrent computation of threads, and distributed computing across multiple processors and systems allows for simultaneous computation. The multiple starting points 1502-1504 are, in best cases, well distributed across the state-space surface, while the secondary points that serve as starting points for threads are more locally distributed about the starting points from which they are computed. The number of starting points and secondary points, as well as the degree to which starting points are separated from one another in the state-space volume, are generally regarded as tunable parameters.

As discussed above, in high-dimensional problem domains, the number of states within even relatively tiny neighborhoods about a given state along a search path can be enormous. One approach to decreasing the number of computations needed for a state-space search would be to decrease the size of a neighborhood analyzed in order to compute a next descent vector. However, as the neighborhood size is decreased, the direction of the descent vector becomes less reliable. Moreover, the effective step distance that can be taken based on a less-reliable descent vector significantly decreases with the neighborhood size used to compute the descent vector. By decreasing neighborhood size, the number of steps needed in an effective search tends to be increased.

Figure 17:
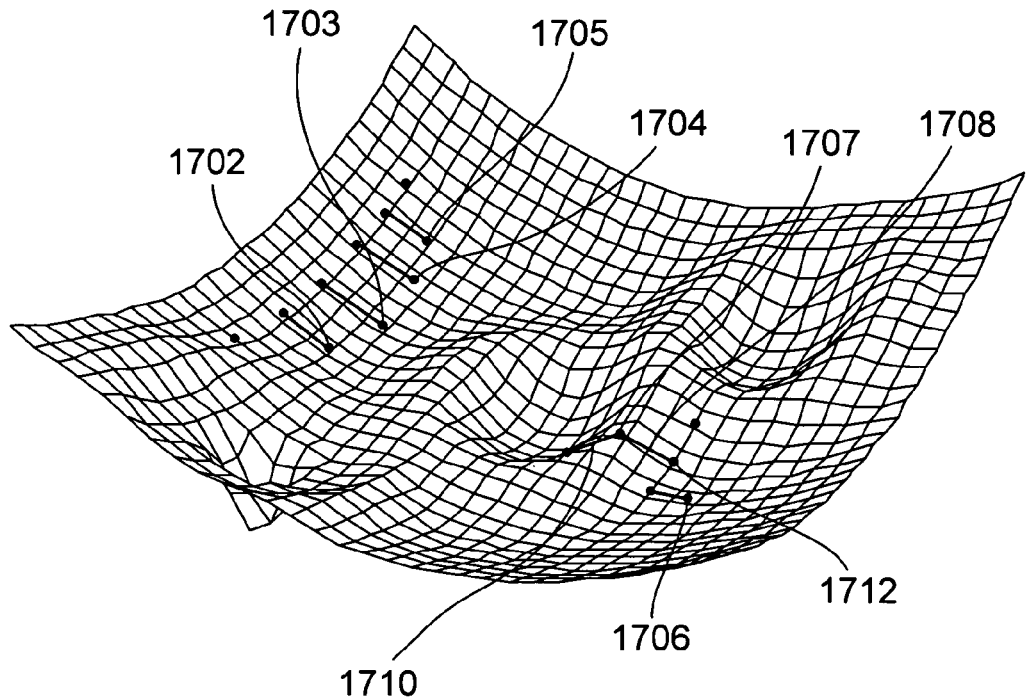

The present optimization method takes a different approach to increasing the computational efficiency of the path search. Rather than decreasing the size of a neighborhood, the present method decreases the dimensionality of the neighborhood, computing at each step a descent vector with respect to some subset of the total number of dimensions, and moving, at each step, generally in the subset of dimensions for which the descent vector is computed. Then, in a subsequent step, a descent vector in a different subset of dimensions is computed, and the search moves generally with respect to the set of dimensions for which the new descent vector is computed. Note that, in the current example, the secondary points illustrated in FIG. 16 lie in a direction roughly parallel with the sequence axis (702 in FIG. 7) with respect to the starting points from which they are calculated. In other words, in the initial step of the optimization, the secondary points are computed only with respect to the sequence axis, and not with respect to both the sequence and conformation axes. As discussed above, the 2n dimensions of the state space, in the current example, are projected onto the two dimensions defined by the sequence axis and the conformation axis (702 and 704 in FIG. 7). Therefore, the multiple secondary points are computed relative to n-dimensional sequence space, a subset of the 2n-dimensional sequence/conformation space. In the next step, shown in FIG. 17, the next points along the paths for each thread are computed with respect to the conformation axis, rather than the sequence axis. As shown in FIG. 17, these next points 1702-1707 lie in directions from the secondary points, from which they were calculated, roughly parallel to the attachments axis.

Figure 18:
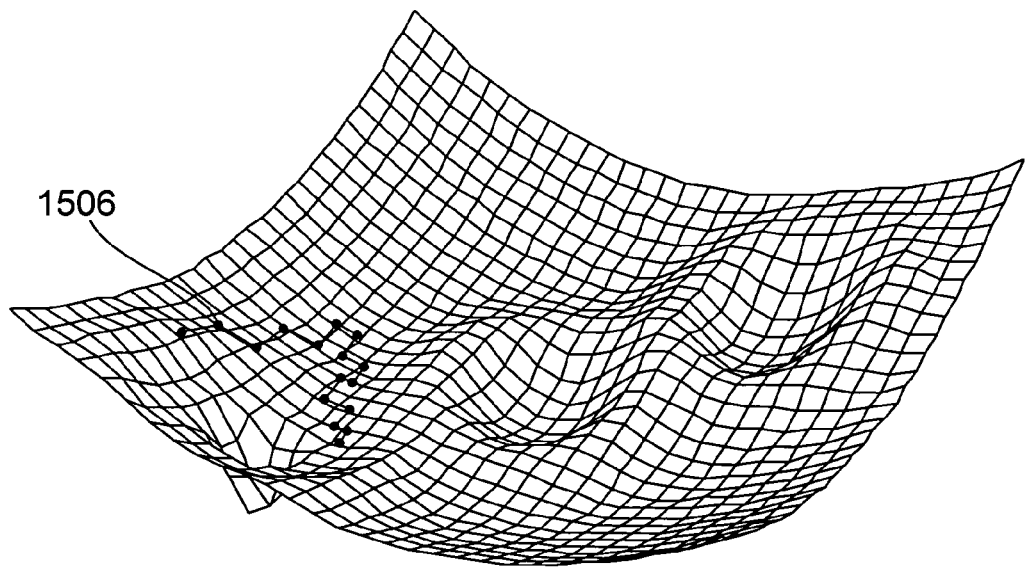

FIG. 18 shows the full search path computed for the thread beginning at point 1506. As seen in FIG. 18, the path consists of moves that alternate, in direction, between a direction parallel to the conformation axis and a direction parallel to the sequence axis. The path resembles the path that an automobile may take when traversing a grid-like arrangement of streets in a city. At each decision point, the automobile may go left, right, or forward. The decisions are greatly reduced from the continuum of direction represented by full 360-degree compass-direction range available to, for example, a crow in flight at each point in flight. The crow can generally traverse the city by flying a shorter distance, but the neighborhood of directions that the crow considers includes far more directions to decide from that the direction selection available to the automobile at each intersection. Similarly, in the present optimization method, the computation of each subsequent move is based on considering a neighborhood of reduced dimensionality, therefore requiring exponentially less computation in order to obtain a reasonably accurate descent vector with respect to a reduced number of dimensions.

This method works best when the dimensions of the problem space are truly separable, so that a change in the values of variables associated with the first dimension partition made during a move with respect to the first dimension partition have little effect on the values of variables associated with all other dimension partitions for points along the move. Also, the cost function needs to provide a reasonable driving force for moves with respect to all dimension partitions. When the dimensions are not separable, then the decrease in dimensionality of considered neighborhoods is analogous to decreasing the neighborhood size in volume, leading only to increasingly unreliable trajectories for moves. There is, in general, a continuity in the degree of separability of problem domains. The method of optimization of the present invention can be effectively used in many cases of partial separability. The fact that, as noted above, component substrings can have different conformations, but identical distances and directions between starting and ending points, indicates that conformation is at least partially separable from sequence.

A final feature of the optimization method used in one embodiment of the present invention is a means for jiggling, or destabilizing, the threads, in each reduced dimensionality descent-vector computation, in order to avoid entrapment of threads by relatively shallow local minima. Referring back to FIG. 17, note that the method has chosen a direction for a third step 1708 in which the cost actually increases. However, by choosing an unfavorable direction in step 1708, in a subsequent step 1710, an exceedingly favorable subsequent direction can be chosen to lead to a local minimum separated from the secondary state by a shallow, positive cost ridge 1712.

In summary, the optimization method used in one embodiment of the present invention employs a number of strategies for a computationally efficient search of a high-dimensional state space. First, multiple starting points are computed. Second, multiple threads are spawned from each of the multiple starting points. With n starting points, and m threads spawned from each of the n starting points, a total of mn independent threads are concurrently, simultaneously, or both concurrently and simultaneously followed by the optimization method, facilitating a comprehensive search that can avoid entrapment by a number of local minima less than mn. Third, and perhaps most importantly, the optimization method alternates, for each thread, between different lower dimensional neighborhoods for choosing directions for a next move. In other words, the method of optimization alternates between choosing the directions of moves with respect to different partitions of the total number of dimensions in the problem domain. By doing so, the computational overhead for computing a next direction is vastly reduced, in high-dimensional problem domains. Finally, the method of the present invention can jiggle, or destabilize, any thread at any particular move, regardless of the dimension partition for which the direction of the move is computed, in order to avoid entrapment of a particular thread in a shallow local minimum of any dimensionality. By this approach, very high-dimensional problem domains can be effectively searched for significant and near-global local minima in reasonable time periods.

Method and System for Designing a Sequence to Produce a Polypeptide with an Initially Specified 3-Dimensional Conformation The general method of optimization described in the previous subsection can be effectively employed to optimize amino-acid sequences and conformations of polypeptides in order to find an optimal sequence for a polypeptide that adopts an initially specified 3-dimensional conformation in a specified chemical environment. In one embodiment of the present invention, discussed below, the length of the desired polypeptide and structural and sequence constraints for the desired polypeptide are initially specified, and the state space of possible sequence/conformations of polypeptides the specified length is searched in order to find one or more sequences that produce the initially specified 3-dimensional conformation in solution. The sequence/conformation search is driven, or directed, by the free energy computed for the 3-dimensional conformations of the peptides with selected sequences. In other words, the sequence/conformation space search is an optimization problem in which free energy is optimized.

Figure 19:
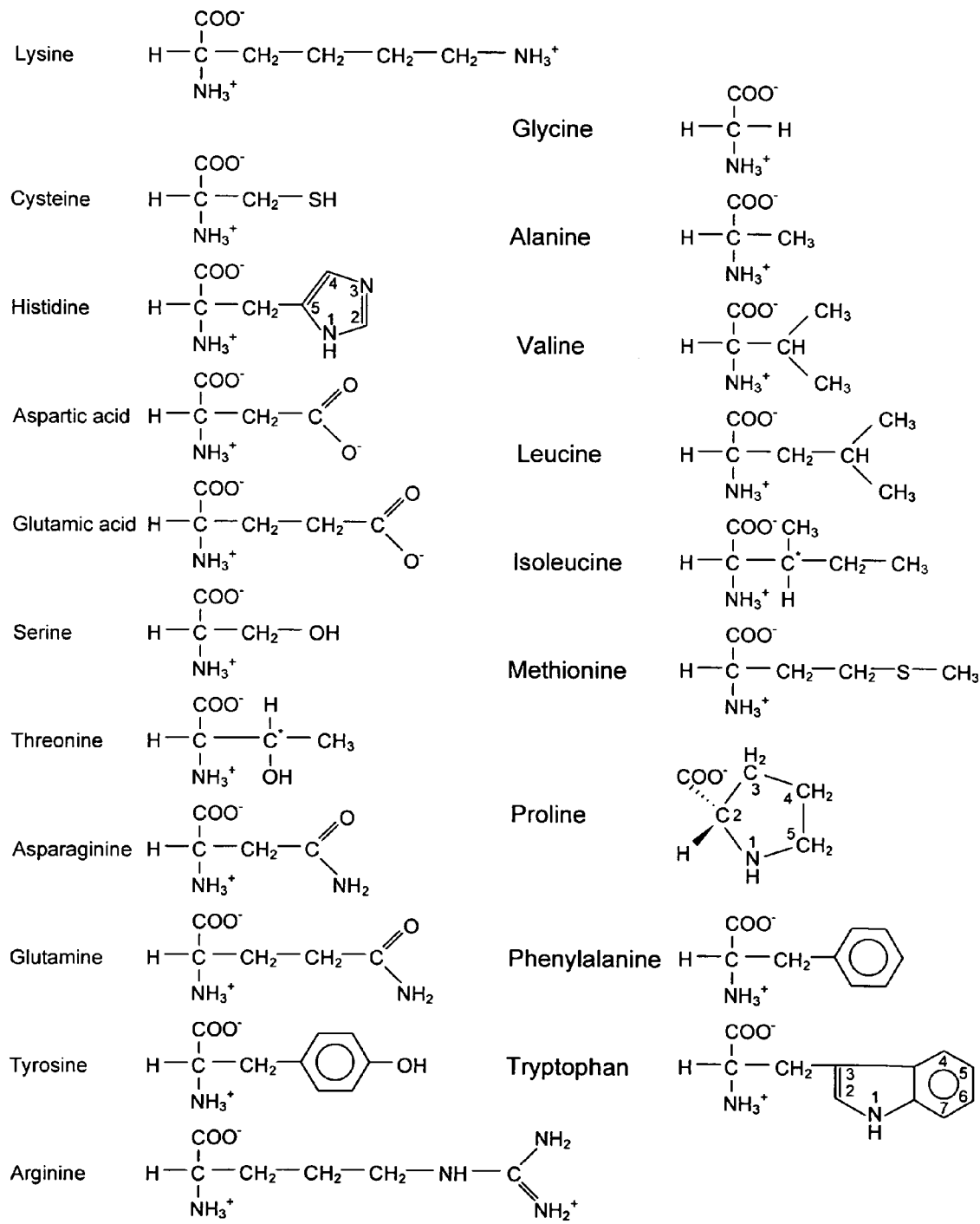
FIG. 19 shows the chemical structures of the 20 amino acids commonly encountered in polypeptides of biological origin.

First, a concise review of polypeptides is provided, to facilitate appreciation of the variables, or dimensions, of the problem domain. Polypeptides are linear polymers of amino acid monomers, formed both naturally and artificially by condensation reactions that produce an amide linkage of the alpha-amino group of a newly added amino acid to the terminal carboxyl group of a growing polypeptide and production of a molecule of water. FIG. 19 shows the chemical structures of the 20 amino acids commonly encountered in polypeptides of biological origin. A number of additional amino acids are less frequently encountered in polypeptides of biological origin, most synthesized in living organisms by enzyme-catalyzed modification of the commonly occurring amino acids.

Figure 20:
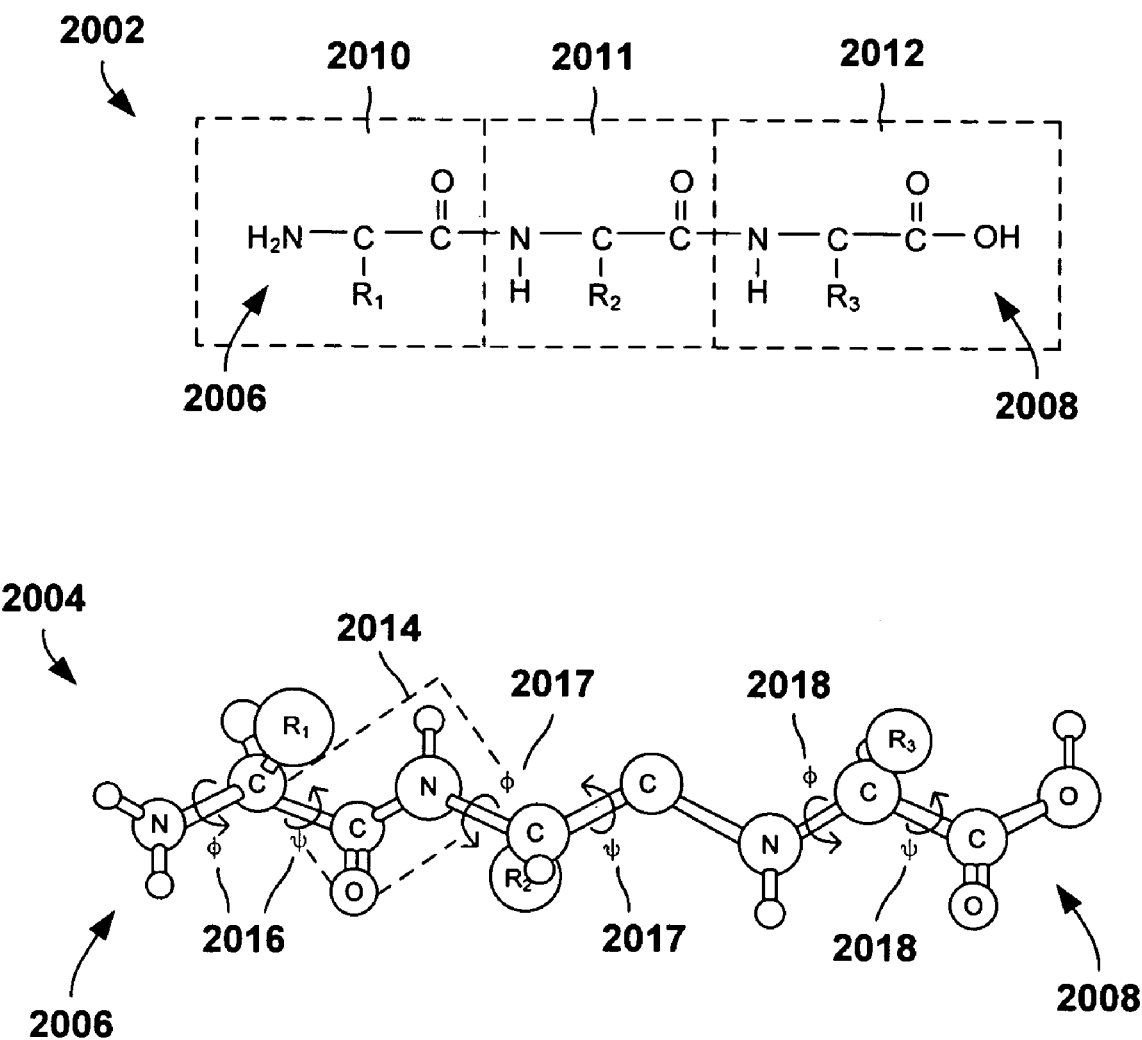
FIG. 20 illustrates a 3-amino-acid polypeptide.

FIG. 20 illustrates a 3-amino-acid polypeptide. In FIG. 20, the chemical formula 2002 for the 3-amino-acid polypeptide is shown aligned with a ball-and-stick representation 2004 of the polypeptide. The symbols "$R_1$," "$R_2$," and "$R_3$" in both the chemical formula 2002 and the ball-and-stick model 2004 stand for the side chain structures of the amino acids, those portions of the amino acid molecule not involved in peptide linkages. In other words, both the chemical formula 2002 and the ball-and-stick representation 2004 emphasize the peptide linkages that form the polypeptide backbone, rather than the complete structural formula for the amino acid side chains. The polypeptide has an N-terminal end 2006 and a carboxyl terminal end 2008. Dashed lines superimposed over the structural formula 2002 indicate the collection of atoms belonging to each of the three amino acid monomers 2010-2012, or residues, that together compose the polypeptide. Because of the electronic states and molecular orbital geometries of the polypeptide backbone, each peptide group, an example of which is indicated by the dashed square 2014 in the ball-and-stick representation 2004, is relatively planer. Thus, the 3-dimensional conformation of a polypeptide backbone is nearly completely specified by the torsion angles of only two types of covalent bonds: (1) the alpha-carbon/alpha-amino-nitrogen bonds, referred to as the $\Phi$ torsion angles; and (2) the alpha-carbon/alpha-carboxyl-carbon bond, referred to as the $\Psi$ torsion angle. Thus, the backbone conformation of the 3-amino-acid polypeptide shown in FIG. 20 is specified by the numerical values for three $\Phi/\Psi$ torsion angle pairs 2016-2018.

Figure 21:
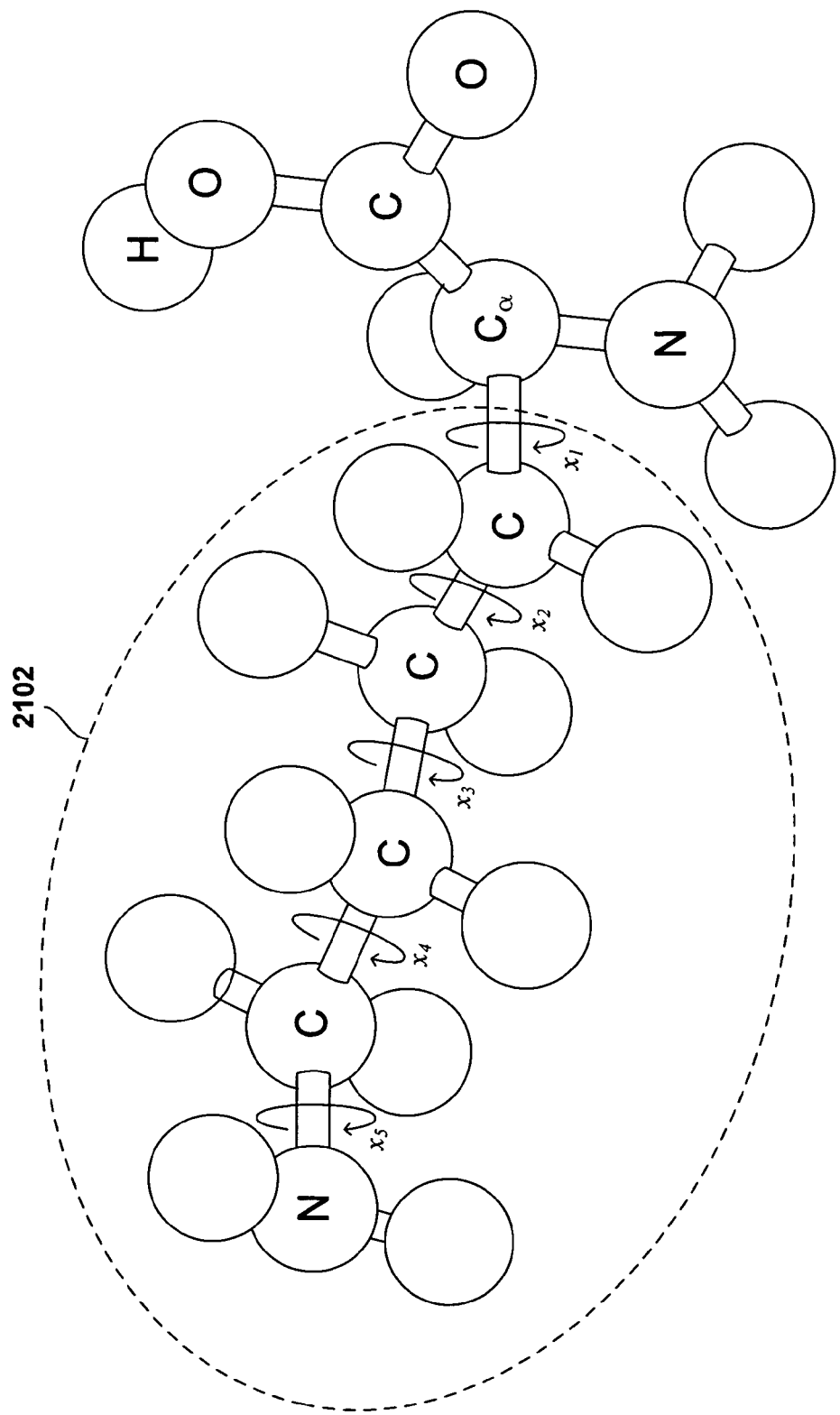
FIG. 21 shows a ball-and-stick representation of the free amino acid lysine.

FIG. 21 shows a ball-and-stick representation of the free amino acid lysine. The group of atoms surrounded in FIG. 21 by the dashed line 2102 is the side chain, or R group, for the amino acid lysine. The torsion angles labeled $X_1$-$X_5$ that specify the rotations about the carbon-carbon and single carbon-nitrogen bonds fully specify the 3-dimensional conformation of the lysine side chain. The full, atomic-level, 3-dimensional conformation of a polypeptide is determined by the sequence of amino acid types along the polypeptide and by the $\Phi, \Psi$, and X torsion angles for each peptide group and side chain. Each different amino acid has a different set of X-angle types.

Many naturally occurring globular proteins comprise either single polypeptides folded into a native, stable conformation, held together by non-covalent bonds, including ionic bonds, Van der Waals forces, hydrogen bonds, covalent disulphide bonds, and favorable entropy changes associated with association of hydrophobic side chains. Additional naturally occurring proteins comprise multiple polypeptides, each in a stable 3-dimensional conformation, held together by many of the forces that determine the conformations of single polypeptides. Globular proteins generally have one or a few stable conformations in any particular chemical environment, and the conformations are often quite complex.

Figure 22A:
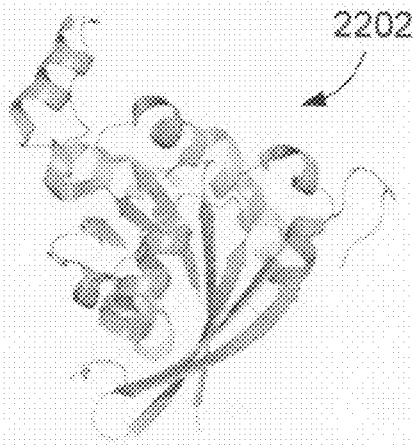
FIGS. 22A-C shows three different representations of the 3-dimensional structure of the myoglobin protein.
Figure 22B:
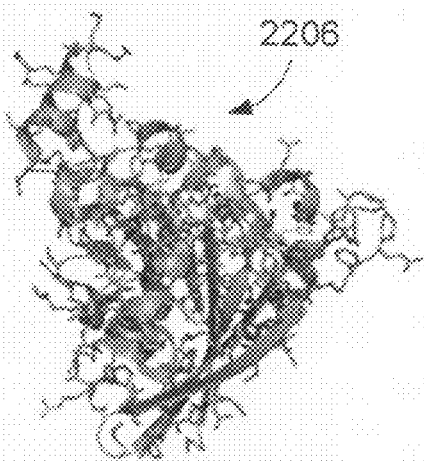
Figure 22C:
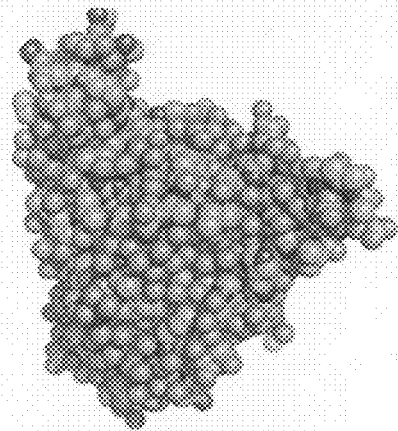

FIGS. 22A-C show three different representations of the 3-dimensional structure of the myoglobin protein. Myoglobin is a single polypeptide consisting of 153 amino-acid residues. FIG. 22A shows a ribbon-and-loop representation of the backbone of the myoglobin molecule. FIG. 22B shows the ribbon-and-loop representation of the backbone polypeptide along with ball-and-stick representations of selected side chains and the heme prosthetic group. FIG. 22C shows the 3-dimensional structure of the myoglobin molecule using spherical atomic representations that approximate the Van der Waals radius of the individual atoms within the molecule. The 3-dimensional conformation of a protein, such as myoglobin, represents a low free-energy state of the molecule. Free energy, denoted G, is a thermodynamic quantity representing the chemical energy of a system. In the current context, the free energy represents the chemical energy of a system comprising a globular protein molecule and its aqueous environment. Formation of hydrogen bonds, ionic bonds, and Van der Waals attractive forces contribute to lowering the enthalpy of the molecule, and association of hydrophobic portions of the molecule and exclusion of water from those hydrophobic regions contributes to an increase in entropy. Both a decrease in enthalpy and an increase in entropy lead to a decrease in free energy.

Examination of many 3-dimensional structures determined for various globular proteins has revealed that there are certain common motifs, or regions of secondary structure, that commonly occur in stable protein conformations. One example is the $\alpha$-helix, often shown as a helical ribbon, such as $\alpha$-helix 2206 in FIG. 22B, in backbone representations of protein structures. Other common motifs include $\beta$ sheets, $\beta$ barrels, and particular types of transitions between $\alpha$ helices and particular types of $\beta$ regions. A particular amino acid monomer within a polypeptide can be considered to occupy an absolute position with respect to the polypeptide sequence, as well as occupying a relative position within a particular type of secondary structure.

Any calculation of the free energy of a conformation of a complex molecule, such as a polypeptide, necessarily involves many approximations. Calculation of free energy by the most exact methods possible would, by itself, be a very computationally intensive task. Therefore, in order to make the sequence-design problem computationally tractable, an approximation method for computing the free energy of a conformation must be carefully selected to provide sufficient accuracy to drive, or direct, the optimization problem to a reasonable minimal-free-energy conformation, but also to be computable within a relatively short time and with expenditure of a minimal number of processing cycles. For the problem of sequence design, a sufficiently accurate, but computationally tractable, approximation involves a free-energy calculation in which the free energy is computed as the sum of free-energies associated with atoms and the sum of pair-wise free-energy terms for pairs of atoms in the molecule, or as the sum of free-energies associated with amino acids and the sum of pair-wise free-energy terms for pairs of amino acids in the molecule, depending on the granularity of the approximation needed at a particular point in time. Moreover, the free energy for a particular atom or amino acid is computed as the sum of a free energy for the atom or amino acid and a sum of the pair-wise atom-to-atom or amino-acid-to-amino-acid interactions between the atom or amino acid and all atoms or amino acids within a specified distance, or spherical neighborhood, of the considered atom or amino acid.

Figure 23:
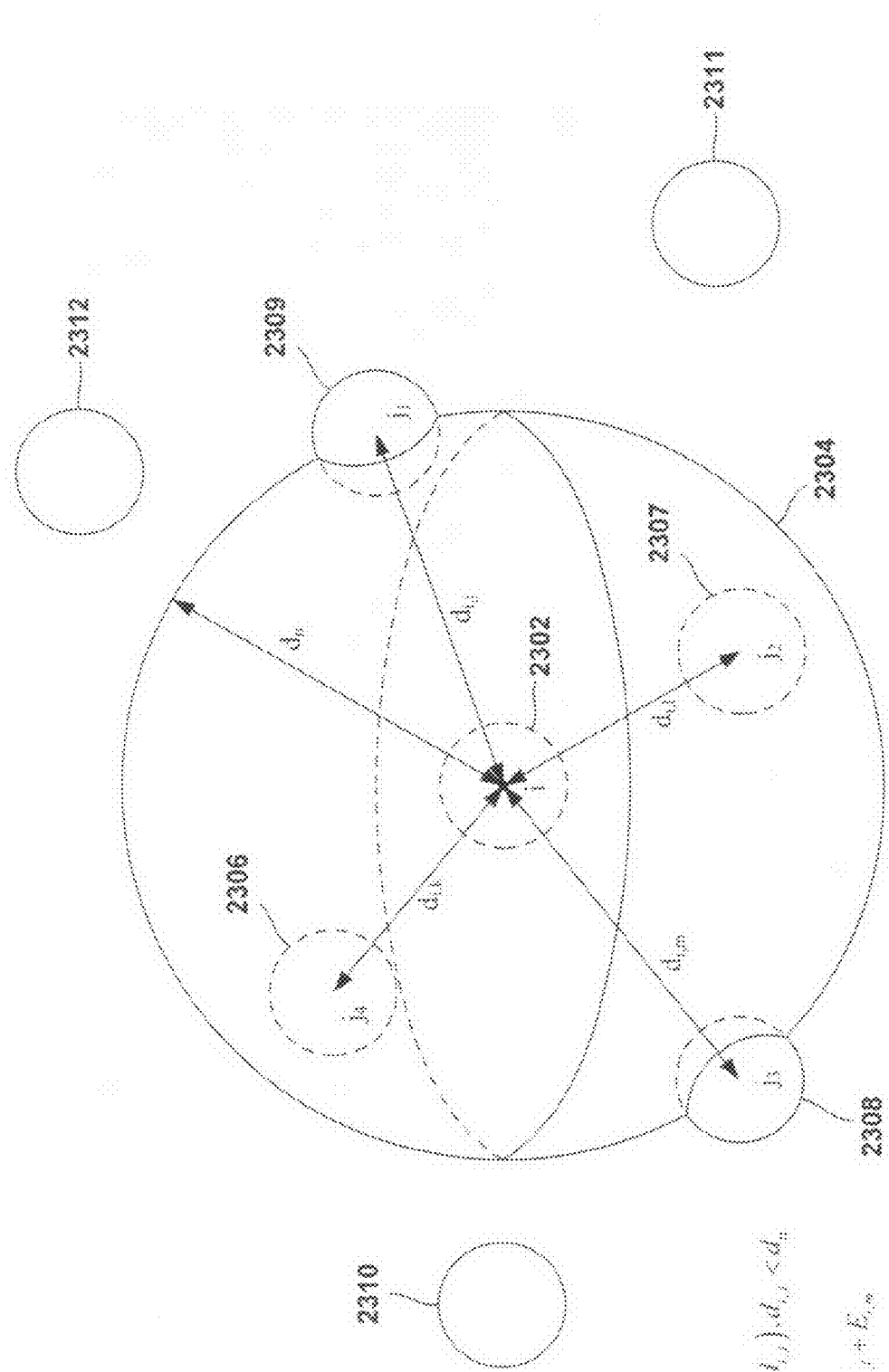
FIG. 23 illustrates the pair-wise energy approximation for computing the free energy of a particular atom in a particular 3-dimensional conformation of a polypeptide.

FIG. 23 illustrates the pair-wise energy approximation for computing the free energy of a particular atom in a particular 3-dimensional conformation of a polypeptide. The considered atom 2302 is considered to be at the center of a spherical neighborhood 2304. Any atom within that spherical neighborhood in the considered polypeptide conformation, including atoms 2306-2309 in FIG. 23, contribute to the approximation of the free energy for the considered atom 2302. Atoms outside the immediate neighborhood, including atoms 2310-2312 in FIG. 23, are not considered to contribute to the free energy for the considered atom. A more exact computation of free energy would include contributions of atoms lying outside the immediate neighborhood, and would also consider higher-order terms involving more than a pair of atoms.

Expressed in general mathematical terms, the free-energy approximation can be stated as:

$$E_{i,j} = \begin{cases} d_{i,j} \leq d_{neighborhood}, f(a_i, a_j, d_{i,j}) \\ d_{i,j} > d_{neighborhood}, 0 \end{cases}$$

$$E_i = f(a_i) + \sum_{j \neq i} E_{i,j}$$

$$E_{polypeptide} = \sum_{i=1}^{N} E_i + \sum_{i=1}^{N} \sum_{j=i+1}^{N} E_{i,j}$$

where $d_{i,j}$=the distance between atoms i and j;

$d_{neighborhood}$=the neighborhood radius, as shown in FIG. 23;

$f(a_i, a_j, d_{i,j})$=a function that depends on the types of atoms i and j, $a_i$ and $a_j$;

$f(a_i)$=a function that depends on the type of atom i;

$E_{i,j}$=the approximate free energy term for interaction of atoms i and j;

$E_i$=the approximate free energy for atom i; and $E_{polypeptide}$=the approximate free energy for a protein molecule.

Note that, in the above expression, amino acids may be considered, rather than atoms, with corresponding functions and distances appropriate for amino acids substituted for those appropriate for atoms. Note also that free energy is generally a relative term, and the sequence-design method computes relative free energy changes for various amino acid substitutions and conformational perturbations during the search of sequence space.

The free energy function that is used in one embodiment of the present invention is expressed as:

$$E_{protein} = W_{rot}E_{rot} + W_{aa\backslash\Phi,\Psi}E_{aa\backslash\Phi,\Psi} + W_{rama}E_{rama} + W_{atr}E_{atr} + W_{rep}E_{rep} + W_{sol}E_{sol} + W_{pair}E_{pair} + W_{bb\_hbond}E_{bb\_hbond} + W_{sc\_hbond}E_{sc\_hbond} + W_{sc\_bb\_hbond}E_{sc\_bb\_hbond} - E_{ref}$$

where W terms are weights, numerical values for which are provided in Table 1, below;

$E_{rot}$ is the energy term for the free energy of the rotamers, discrete, predefined side-chain conformations;

$E_{aa\backslash\Phi,\Psi}$ is the energy term related to $\Phi\Psi$ torsion angles preferred by particular amino acids;

$E_{rama}$ is an energy term related to $\Phi\Psi$ torsion angles favored by particular amino acids within particular types of secondary structure;

$E_{atr}$ is an energy term related to non-covalent attractive forces between atoms, approximated by a Lennard-Jones potential energy function;

$E_{rep}$ is an energy term related to non-covalent repulsive forces between atoms, approximated by a Lennard-Jones potential energy function $E_{pair}$ is an energy term related to probabilities of associations of types of amino acids in 3-dimensional space;

$E_{bb\_hbond}$ is an energy term related to formation of backbone-atom-to-backbone-atom hydrogen bonds;

$E_{sc\_hbond}$ is an energy term related to formation of sidechain-atom-to-sidechain-atom hydrogen bonds;

$E_{sc\_bb\_hbond}$ is an energy term related to formation of sidechain-atom-to-backbone-atom hydrogen bonds $E_{ref}$ is an energy term related to the unfolded free energy of the polypeptide, reference energies for individual amino-acid types listed as weights in Table 1.

TABLE 1

Numerical Values for Weight Terms in Free Energy Approximation Equation

| | |
|---|---|
| $W_{atr}$ | 0.80 |
| $W_{rep}$ | 0.65 |
| $W_{sol}$ | 0.65 |
| $W_{pair}$ | 0.65 |
| $W_{bb\_hbond}$ | 0.80 |
| $W_{sc\_hbond}$ | 1.10 |
| $W_{sc\_bb\_hbond}$ | 1.10 |
| $W\_rot$ | 0.70 |
| $W_{ref}$(Ala) | 0.05 |
| $W_{ref}$(Asp) | 1.43 |
| $W_{ref}$(Glu) | 1.44 |
| $W_{ref}$(Phe) | -1.20 |
| $W_{ref}$(Gly) | 0.37 |
| $W_{ref}$(His) | -1.92 |
| $W_{ref}$(Ile) | -0.45 |
| $W_{ref}$(Lys) | 1.30 |
| $W_{ref}$(Leu) | -1.62 |
| $W_{ref}$(Met) | 0.25 |
| $W_{ref}$(Asn) | 0.17 |
| $W_{ref}$(Pro) | -0.30 |
| $W_{ref}$(Gln) | 0.14 |
| $W_{ref}$(Arg) | 0.60 |
| $W_{ref}$(Ser) | 0.14 |
| $W_{ref}$(Thr) | 0.31 |
| $W_{ref}$(Val) | -0.25 |
| $W_{ref}$(Trp) | -1.85 |
| $W_{ref}$(Tyr) | -1.08 |

The weights for collective energy terms and the reference energies for different amino acids, listed in Table 1, are determined by maximizing the product of $\exp(-E(aa_{obs}))/(\Sigma\exp(-E(aa_i)))$ over a training set of 30 proteins using a conjugate-gradient-based optimization method, where $E(aa_{obs})$ is the energy of the native amino acid at a position and the partition function in the denominator is over all 20 amino acids at each position. In this process, only one residue is changed at a time, and all other residues are kept in their native conformations. The parameters are then refined slightly on the basis of the results of complete redesign calculations on training-set proteins.

It should be noted that the free energy approximation assumes a dilute, aqueous environment. The free energy approximation can be modified to provide free energy approximations for other chemical environments.

To calculate the salvation energy, $E_{sol}$, and the Lennard-Jones energies, $E_{atr}$ and $E_{rep}$, the various atoms of the 20 amino acids are binned into types, shown below in Table 2.

TABLE 2

Atom Types

| Atom Type Number | Atom type description |
|---|---|
| 1 | carbonyl carbon in sidechain of Asn and Gln, and guanidyl carbon in Arg |
| 2 | carboxyl carbon in Asp and Glu |
| 3 | aliphatic carbon with one hydrogen |
| 4 | aliphatic carbon with two hydrogens |
| 5 | aliphatic carbon with three hydrogens |
| 6 | aromatic ring carbon |
| 7 | nitrogen in Trp sidechain |
| 8 | nitrogen in His sidechain |
| 9 | nitrogen in Asn and Gln sidechain |
| 10 | nitrogen in Lys sidechain |

TABLE 2-continued

Atom Types

| Atom Type Number | Atom type description |
|---|---|
| 11 | nitrogen in Arg sidechain |
| 12 | nitrogen in Pro backbone |
| 13 | hydroxyl oxygen |
| 14 | carbonyl oxygen in Asn and Gln sidechains |
| 15 | carboxyl oxygen in Asp and Glu |
| 16 | sulfur in Cys and Met |
| 17 | backbone nitrogen |
| 18 | backbone alpha carbon |
| 19 | backbone carbonyl carbon |
| 20 | backbone oxygen |
| 21 | polar hydrogen |
| 22 | nonpolar hydrogen |
| 23 | aromatic hydrogen |
| 24 | backbone HN |

Lennard-Jones-Potential-Related Terms ($E_{atr}$ and $E_{rep}$)

A standard 12-6 Lennard-Jones potential is used, except there is cutoff distance below which the potential is extrapolated linearly. Favorable energies are placed in $E_{atr}$ and unfavorable energies are placed in $E_{rep}$.

$$E_{atr} = \sum_i^{natom} \sum_{j>i}^{natom} \left[ \left(\frac{r_{ij}}{d_{ij}}\right)^{12} - 2\left(\frac{r_{ij}}{d_{ij}}\right)^{6} \right] e_{ij} \text{ if } \frac{r_{ij}}{d_{ij}} < 1.12$$

$$E_{rep} = \sum_i^{natom} \sum_{j>i}^{natom} \left[ \left(\frac{r_{ij}}{d_{ij}}\right)^{12} - 2\left(\frac{r_{ij}}{d_{ij}}\right)^{6} \right] e_{ij} \text{ if } 1.33 >$$

$$\frac{r_{ij}}{d_{ij}} > 1.12 + \sum_i^{natom} \sum_{j>i}^{natom} y_{intercept} - d_{ij} * slope \text{ if } \frac{r_{ij}}{d_{ij}} > 1.33$$

$$slope = -12 e_{ij} (1.33^{13} - 1.33^{7}) * (1/r_{ij})$$

$$y_{intercept} = -slope * \left(\frac{r_{ij}}{1.33}\right) + e_{ij}(1.33^{12} - 2(1.33)^{6})$$

$$r_{ij} = r_i + r_j$$

$$e_{ij} = \sqrt{e_i e_j}$$

Well depths and radii used for the Lennard-Jones calculations are provided, below, in Table 3. The well depths are those used in the CHARMM19 parameter set. The radii are determined by fitting the Lennard-Jones potential to the distribution of distances observed between the atom types in the PDB.

TABLE 3

Well depths and Radii.

| Atom Type | Radii(r) | well depth (e) |
|---|---|---|
| 1 | 2.00 | 0.1200 |
| 2 | 2.00 | 0.1200 |
| 3 | 2.00 | 0.0486 |
| 4 | 2.00 | 0.1142 |
| 5 | 2.00 | 0.1811 |
| 6 | 2.00 | 0.1200 |
| 7 | 1.75[1] | 0.2384 |
| 8 | 1.75[1] | 0.2384 |
| 9 | 1.75[1] | 0.2384 |

TABLE 3-continued

Well depths and Radii.

| Atom Type | Radii(r) | well depth (e) |
|---|---|---|
| 10 | 1.75[1] | 0.2384 |
| 11 | 1.75[1] | 0.2384 |
| 12 | 1.75[1] | 0.2384 |
| 13 | 1.55[1,2] | 0.1591 |
| 14 | 1.55[2] | 0.1591 |
| 15 | 1.55[2] | 0.2100 |
| 16 | 1.90 | 0.1600 |
| 17 | 1.75 | 0.2384 |
| 18 | 2.00 | 0.0486 |
| 19 | 2.00 | 0.1400 |
| 20 | 1.55 | 0.1591 |
| 21 | 1.00[3] | 0.0500 |
| 22 | 1.20 | 0.0500 |
| 23 | 1.20 | 0.0500 |
| 24 | 1.00[3] | 0.0500 |

[1]These atom types are hydrogen bond donors and, when paired with atom types that are hydrogen bond acceptors, $r_{ij}$ is set to 2.95, the optimal distance for hydrogen bonding. This is to prevent the repulsive portion of the Lennard-Jones term from disfavoring hydrogen bonds.
[2]These atom types are hydrogen bond acceptors and, when paired with atom types that are hydrogen bond donors, $r_{ij}$ is set to 2.95.
[3]These are polar hydrogens and, when paired with hydrogen bond acceptors, $r_{ij}$ is set to 1.95.

Figure 24:
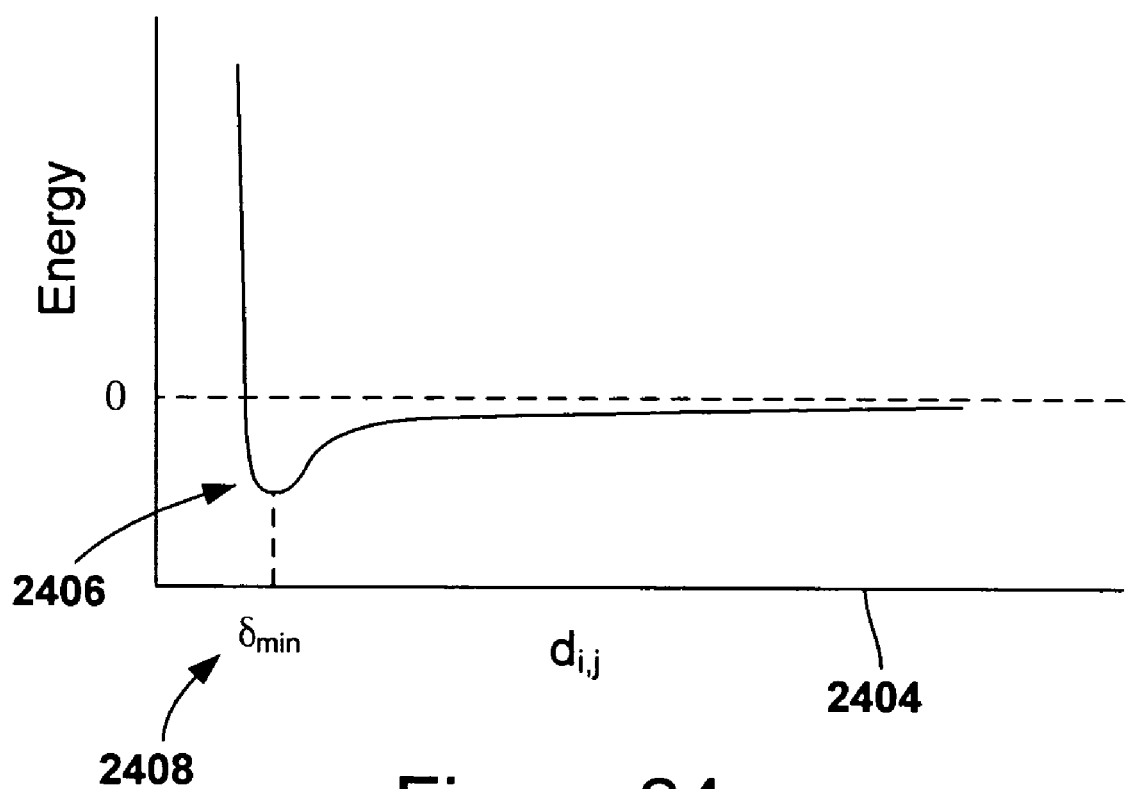
FIG. 24 shows a representation of the Lennard-Jones potential function.

A Lennard-Jones potential is often displayed as a 2-dimensional graph of potential energy versus distance between atoms. FIG. 24 shows a representation of the Lennard-Jones potential function. The vertical axis is energy, and the horizontal axis 2404 is distance between atoms i and j. Regardless of the types of atoms concerned, the Lennard-Jones potential normally shows a significant potential energy well 2406. The energy rapidly rises as the inter-atomic distance decreases from the energy minimum, and rises, at first rapidly, and then more gradually, approaching a potential energy of 0, as the atoms become further separated in space. The distance corresponding to the minimum potential energy represents the most probable inter-atomic distance for a pair of atoms i and j. Note that the exact form and minimum distance depends on the types of the two atoms.

Lazaridis-Karplus Solvation Model ($E_{solv}$)

An implicit solvation model, developed by Lazaridis and Karplus, is used to evaluate the solvation energy of a protein:

$$E_{solv} = \sum_i^{natom} \sum_{j>i}^{natom} \left\{ \frac{-2\Delta G_i^{free}}{4\pi\sqrt{\pi} \lambda_i r_{ij}^2} \exp(-d_{ij}^2) V_j - \frac{2\Delta G_i^{free}}{4\pi\sqrt{\pi} \lambda_i r_{ij}^2} \exp(-d_{ji}^2) V_i \right\}$$

where
  $d_{ij}$ and $r_{ij}$ are the same as in $E_{atr}$,
  $\Delta G^{free}$ is related to the solvation energy of the fully solvated atom,
  $\lambda_i$ is a correlation length, and
  V is atomic volume.

The values for the parameters, shown below in Table 4, are taken from Lazaridis and Karplus, except that some of the $\Delta G^{free}$ values have been perturbed to better reproduce the relative frequencies at which amino acids are placed in the core of globular proteins versus being placed in the surface during design experiments. The intrinsic solvation energy of each atom is omitted, because the sum of these values is a constant for each amino acid and can be incorporated into the reference energies, shown above as weights in Table 1.

TABLE 4

Solvation Model Parameters

| Atom Type | $\Delta G^{free}$ | V | $\lambda$ |
|---|---|---|---|
| 1 | 0.00 | 14.7 | 3.5 |
| 2 | −1.40 | 8.3 | 3.5 |
| 3 | −0.25 | 23.7 | 3.5 |
| 4 | 0.52 | 22.4 | 3.5 |
| 5 | 1.50 | 30.0 | 3.5 |
| 6 | 0.08 | 18.4 | 3.5 |
| 7 | −8.9 | 4.4 | 3.5 |
| 8 | −4.0 | 4.4 | 3.5 |
| 9 | −7.8 | 11.2 | 3.5 |
| 10 | −20.0 | 11.2 | 6.0 |
| 11 | −11.0 | 11.2 | 6.0 |
| 12 | −1.55 | 0.0 | 3.5 |
| 13 | −6.77 | 10.8 | 3.5 |
| 14 | −7.8 | 10.8 | 3.5 |
| 15 | −10.0 | 10.8 | 6.0 |
| 16 | −4.1 | 14.7 | 3.5 |
| 17 | −5.0 | 4.4 | 3.5 |
| 18 | 1.00 | 23.7 | 3.5 |
| 19 | 1.00 | 14.7 | 3.5 |
| 20 | −5.00 | 10.8 | 3.5 |
| 21 | 0.00 | 0.0 | 3.5 |
| 22 | 0.00 | 0.0 | 3.5 |
| 23 | 0.00 | 0.0 | 3.5 |
| 24 | 0.00 | 0.0 | 3.5 |

Rotamer-Related Energy Term $E_{rot}$ is related to the self-energy of a rotamer, and is derived from Protein Data Bank statistics by observing the probability of a particular rotamer and amino acid for a given $\Phi$ angle and $\Psi$ angle. $E_{rot}$ is expressed as:

$$E_{rot} = \sum_{i}^{nres} -\ln(P(rot(i) \mid phi(i), psi(i)))$$

The probabilities are taken directly from Dunbrack and Cohen. During the final design simulations, rotamers with X angles perturbed from the most commonly observed X angles (+/−0.5 standard deviation). These sub-rotamers were penalized by assuming a gaussian distribution about the mean using tabulated variances from Dunbrack and Cohen.

Amino Acid Preferences for Particular Regions of $\Phi$, $\Psi$ Space ($E_{aa|\Phi,\Psi}$)

A non-redundant set of PDB files are used to determine the probabilities for observing each of the 20 amino acids within 10°×10° bins in $\Phi,\Psi$ space, P(aa, $|\Phi,\Psi$). The energy as calculated by taking the negative log of the probabilities.

Amino Acid Dependent Torsion Potential for $\Phi$ and $\Psi$ ($E_{rama}$)

For each of the 20 amino-acid types in each of three secondary structure types (helix, strand, and other, as defined by DSSP), the frequency of $\Phi,\Psi$ pairs is determined for 10°×10° bins. Probabilities are calculated using added pseudocounts, and the potential calculated by taking the log of the interpolated probabilities.

Residue Pair Potential ($E_{pair}$)

$E_{pair}$ is derived from the probability of seeing two amino acids close together in space in the PDB database after accounting for the intrinsic probabilities of these amino acids to be in that environment, and is expressed as:

$$E_{pair} = \sum_{i}^{nres} \sum_{j>i}^{nres} \frac{P(aa_i, aa_j \mid d_{ij}, env_i, env_j)}{P(aa_i \mid d_{ij}, env_i) P(aa_j \mid d_{ij}, env_j)}$$

Two classes of environments are considered, buried and exposed, and five distance bins were used, 0-4.5, 4.5-6.0, 6.0-7.5, 7.5-9.0 and 9.0-10.5. This term is only evaluated between polar amino acids. The distances are measured between the action centers on each residue, e.g. the nitrogen on the lysine sidechain.

Orientation-Dependent Hydrogen Bonding Term ($E_{bb\_hbond}$, $E_{sc\_hbond}$, $E_{bb\_sc\_hbond}$)

The energies of backbone-backbone, sidechain-backbone and sidechain-sidechain hydrogen bonds are determined using a function derived from the distances and angles observed for naturally occurring hydrogen bonds in the PDB database. This function is described in detail in the supporting material of Kortemme & Baker. The strengths of the hydrogen bonds are not weighted according to their degree of burial, in order to encourage hydrogen bonds at positions that are partially buried.

Energy of the Unfolded State ($E_{ref}$)

To approximate the energy of the unfolded state, each amino acid is assigned an empirically determined reference energy, as expressed by:

$$E_{ref} = \sum_{i}^{nres} W_{ref}(aa(i))$$

Polypeptides and polypeptide conformations having been discussed, above, in overview, and the free-energy approximation having been provided in detail, above, the method for polypeptide sequence design that represents one embodiment of the present invention can now be described, in detail. This method bears a not coincidental similarity to the component-string problem introduced in a previous subsection. However, the amino-acid-sequence-design problem for a polypeptide sequence of length n is of much higher dimensionality and complexity than an analogous component-sequence-design problem for a component string of length n. First, there are at least 20, rather than three, different types of potential sequence members in the amino-acid-sequence-design problem. Second, the conformations are 3-dimensional, rather than 2-dimensional. Finally, the optimization criterion, free energy, involves a significantly more complex calculation than summing the costs of components and attachments in a component string. However, the method for sequence design of polypeptides to achieve polypeptides that adopt an initially specified 3-dimensional conformation is quite similar to the method used for the component-string problem, and falls into the class of high dimensional optimization problems discussed in the first subsection. First, multiple starting points and multiple threads per starting point are employed in order to concurrently, simultaneously, or both concurrently and simultaneously seek optima in different regions of the sequence/conformation space. Second, the full dimensionality of the problem space is partitioned, and moves are alternatively computed with respect to dimension partitionings. In iterative cycles, the backbone conformation is locally optimized for a particular sequence, and the sequence is then modified with respect to the current backbone conformation.

In both cases, the optimization criterion is the computed free energy change; in the first case, the free energy change for a backbone-conformation modification, and, in the second case, the free energy change for a sequence modification. Finally, an optimization technique is used that allows for local, non-optimal moves in order to avoid thread entrapment by shallow local minima. In one embodiment, a Metropolis Monte Carlo optimization method is used, with selected temperature parameters, that allows for positive free energy changes to occur with some frequency, so that shallow depressions in the free-energy surface can be ascended in order to explore minima lying beyond on the sequence/conformation surface.

Figure 25:
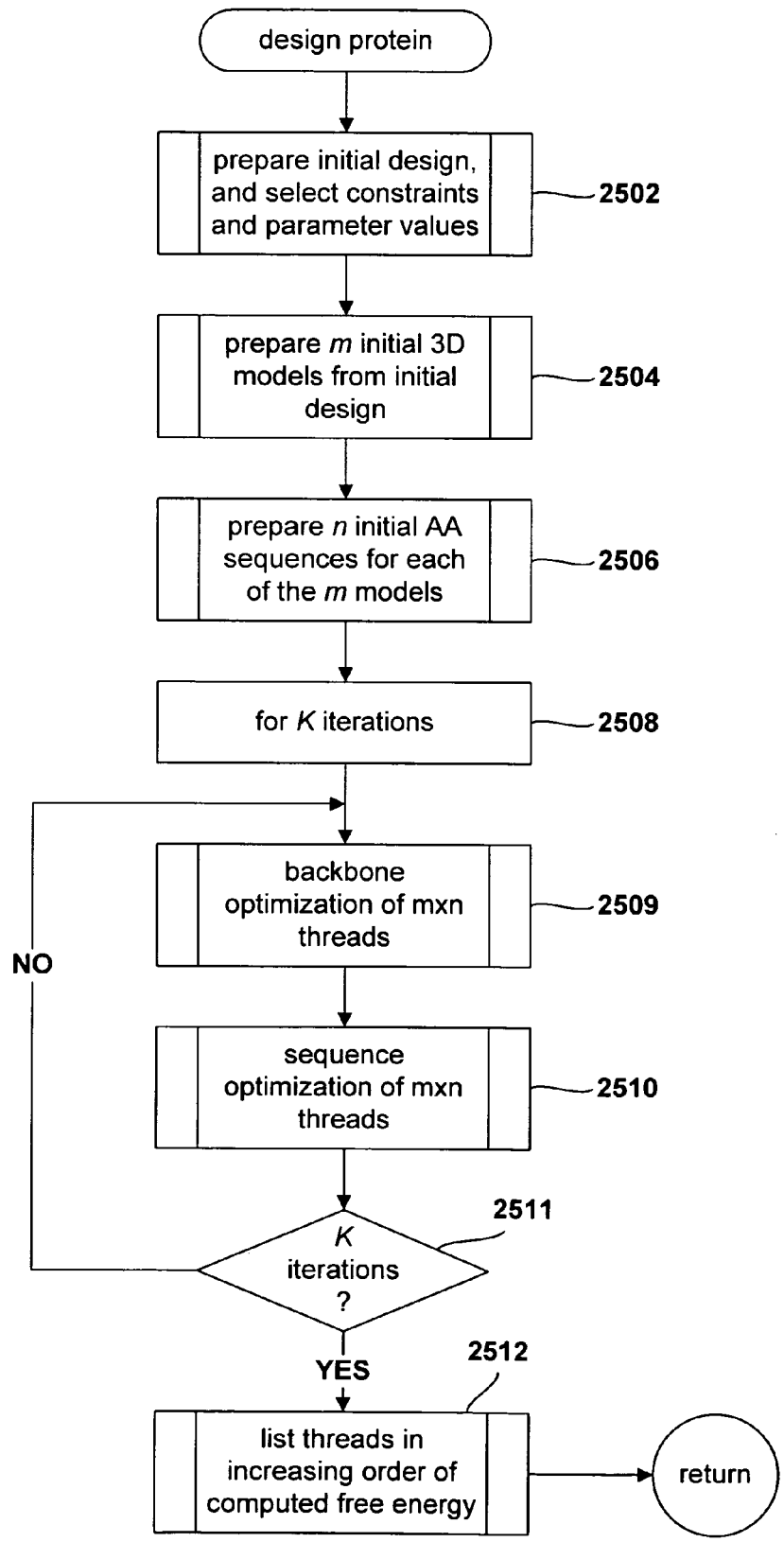
FIG. 25 is a control-flow diagram of the high-level routine "design protein."

FIG. 25 is a control-flow diagram of the high-level routine "design protein." In a first step 2502, an initial target conformation design is prepared, and various types of sequence and conformational constraints are specified. In addition, values for a large set of tunable parameters are chosen in order to apply reasonable time and computational constraints. Next, in step 2504, m different initial 3-dimensional backbone conformations are prepared, representing m discrete starting points, where m is a tunable parameter. Then, in step 2506, n different initial amino-acid sequences for each of the m models are computed, where n is a tunable parameter. Therefore, following step 2506, mn different threads are initialized. Then, in the for-loop of steps 2508-2511, the threads are concurrently, simultaneously, or concurrently and simultaneously optimized for free energy by repeatedly optimizing the backbone conformation, in step 2509, followed by optimizing the amino-acid sequence, in step 2510. The for-loop continues for k iterations, where k is a tunable parameter. In alternative embodiments, the loop may be continuously iterated until various convergence criteria are met. Finally, in step 2512, the resulting sequences obtained by optimizing the sequences of each thread are listed, in increasing order of computed free energy, with the first-occurring, lowest-free-energy sequence most likely to produce a polypeptide that adopts the initially specified 3-dimensional conformation in the chemical environment for which the free-energy computations are directed.

Figure 26:
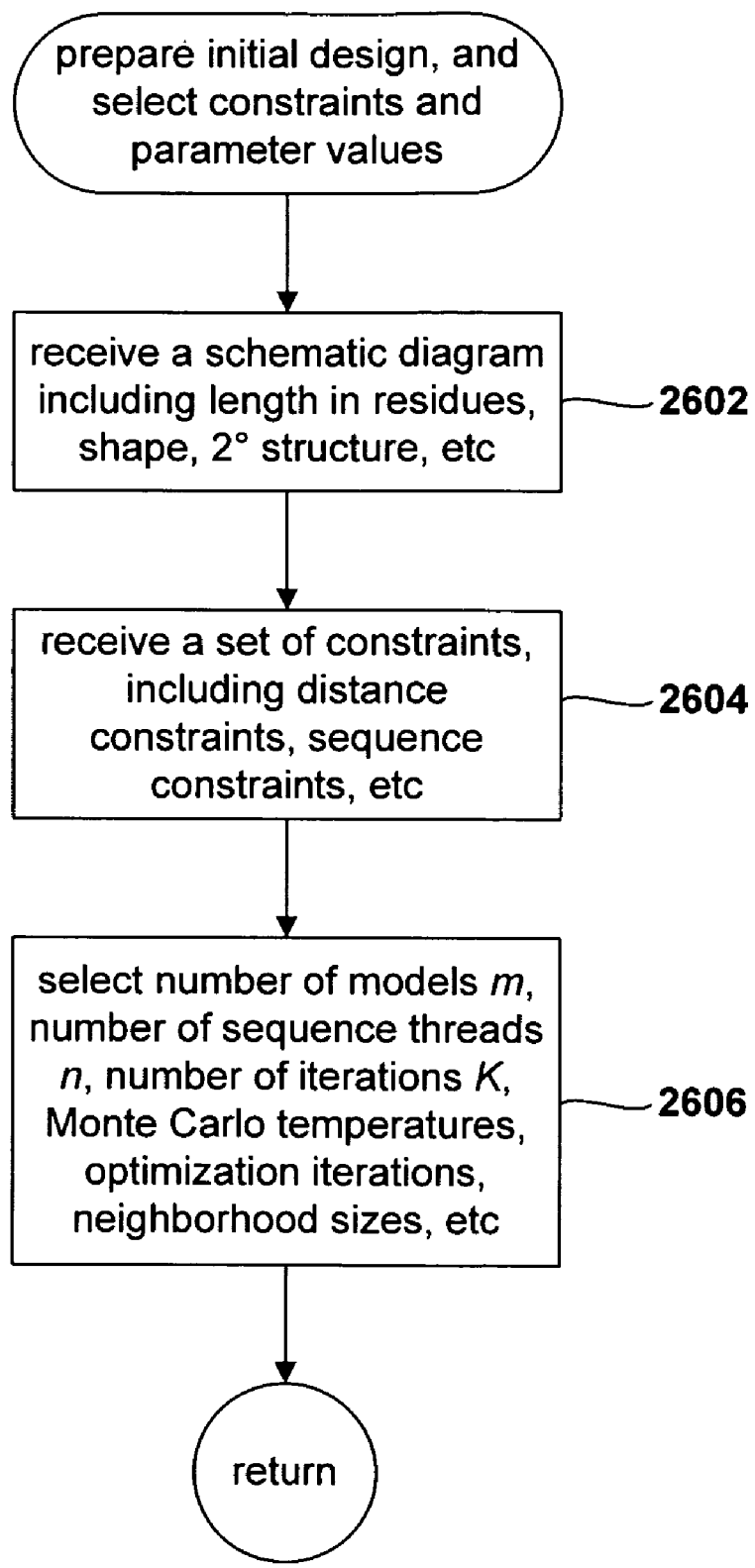
FIG. 26 is a control-flow diagram for the initial step (2502 in FIG. 25) of the routine "design protein."

FIG. 26 is a control-flow diagram for the initial step (2502 in FIG. 25) of the routine "design protein." In a first step, a schematic diagram is received that specifies the desired 3-dimensional conformation of a polypeptide, the length, in residues, of the polypeptide, and various shape constraints, distance constraints, secondary-structure constraints, sequence constraints, and other constraints. Various different embodiments of the present invention employ various different methods for preparing the desired, target conformation specification. For example, certain embodiments employ a graphical user interface that allows a user to select and orient various 3-dimensional conformation components into a desired 3-dimensional conformation, much as graphical user interfaces in various types of chemistry-related applications allow users to construct organic-molecule representations and biopolymer representations by selecting and attaching together graphically represented components, such as atoms and bond types. In alternative embodiments, the 3-dimensional target conformation may be specified as a partial or complete list of atomic coordinates, or may include a list of 3-dimensional-conformation-specifying primitives in a formal conformation-specification language. Next, in step 2604, a set of additional constraints, including distance constraints, sequence constraints, and other constraints, may be received. In various alternative embodiments, the constraints can be specified through a graphical user interface, a text file, or by other means. Finally, in step 2606, the values for the many different tunable parameters are selected, including the number of initial models, or starting points, m, the number of sequence threads to be computed for each initial model, n, the number of overall iterations for thread-sequence optimization k, Monte Carlo temperatures for the Metropolis-Monte-Carlo-based backbone and sequence optimizations, numbers specifying the number of Metropolis-Monte-Carlo-optimization steps, various neighborhood sizes for computing free energies, for relaxing backbone-conformation perturbations, and other neighborhoods, and a variety of other tunable parameters.

Figure 27:
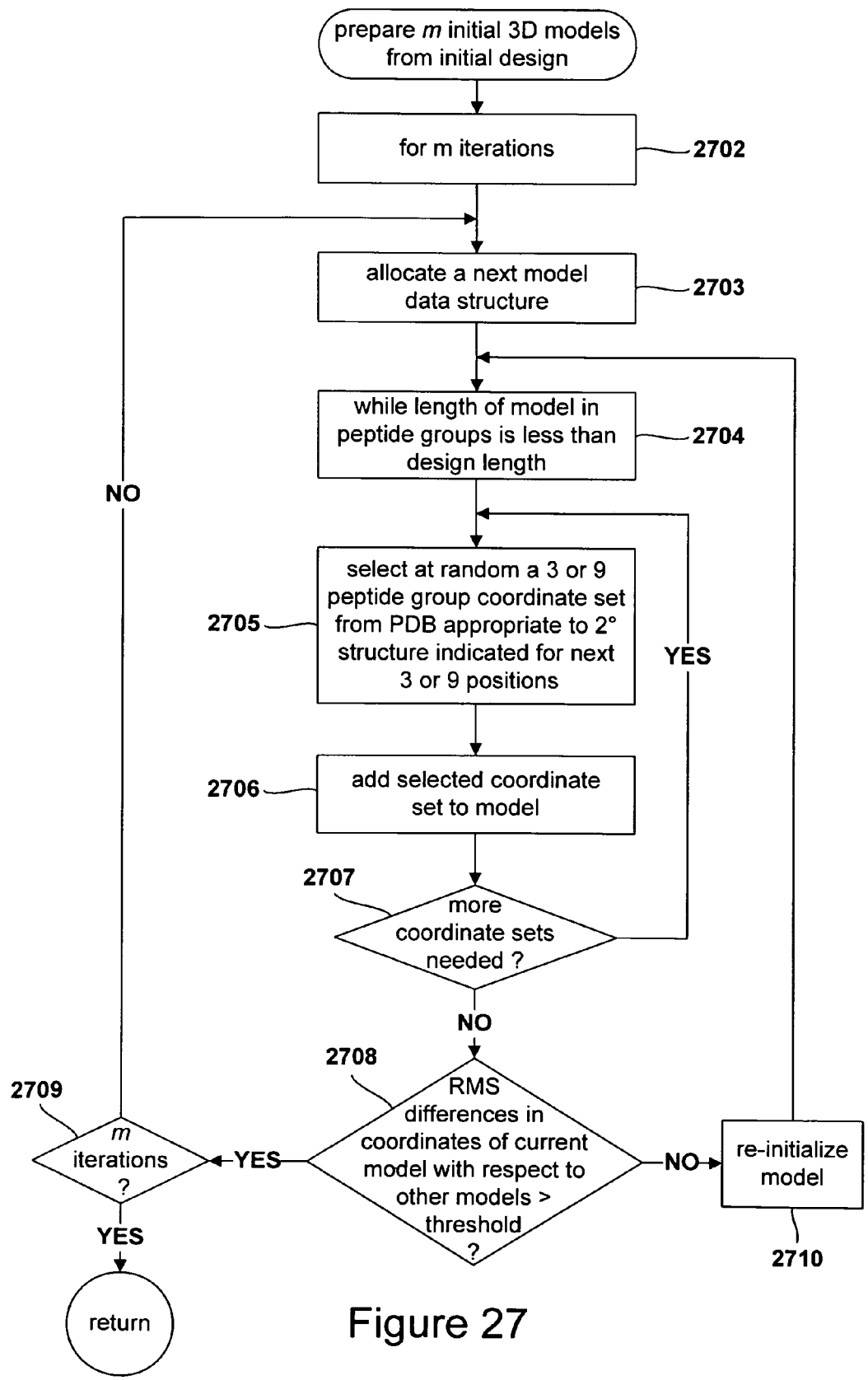
FIG. 27 is a control-flow diagram for the second step (2504 in FIG. 25) of the routine "design protein."

FIG. 27 is a control-flow diagram for the second step (2504 in FIG. 25) of the routine "design protein." In this high-level step, m different initial backbone-conformation starting points are computed. Thus, m iterations of the for-loop comprising steps 2702-2710 are carried out, one iteration per model. First, in each iteration, a data structure for the next model, or currently constructed model, is allocated in step 2703. Then, in the while-loop comprising steps 2704-2707, the coordinates for the backbone of the next model are computed. In step 2705, the backbone coordinates for the next 3 or 9 residues of the model are computed by randomly selecting peptide groups of lengths 3 or 9 residues from the protein databank ("PDB") in regions of secondary structure equivalent to the secondary structure specified in the initial target conformation for the next 3 or 9 residues of the model. In step 2706, these backbone coordinates, or $\Phi\Psi$ torsion angles, are used to specify the conformations of the next 3 or 9 residues of the model. Of course, a number of residues different than 3 and 9 may be needed for the final residues of the model, depending on the length of the model. Moreover, a smaller number of residues may be constructed in a given iteration of the while-loop for portions of the model that include a transition from one type of secondary structure to another.

When the torsion angles for the entire polypeptide background for the currently constructed model have been completely specified, the route-mean-square ("RMS") differences between the backbone conformation for the currently constructed model and the background coordinates for all previously constructed models are then computed, and the currently constructed model is accepted only when the RMS differences between the currently constructed model and previously constructed models is greater than some threshold value, in step 2708. When the threshold criteria is met, then the for-loop is either continued, to create additional models, or, when m models have been constructed, the step is complete, as determined in step 2709. Otherwise, the currently constructed model is re-initialized, in step 2710, and the while-loop of steps 2704-2707 is re-executed. Step 2708 guarantees that the initial models are reasonably well separated from one another in sequence/conformation space.

Figure 28:
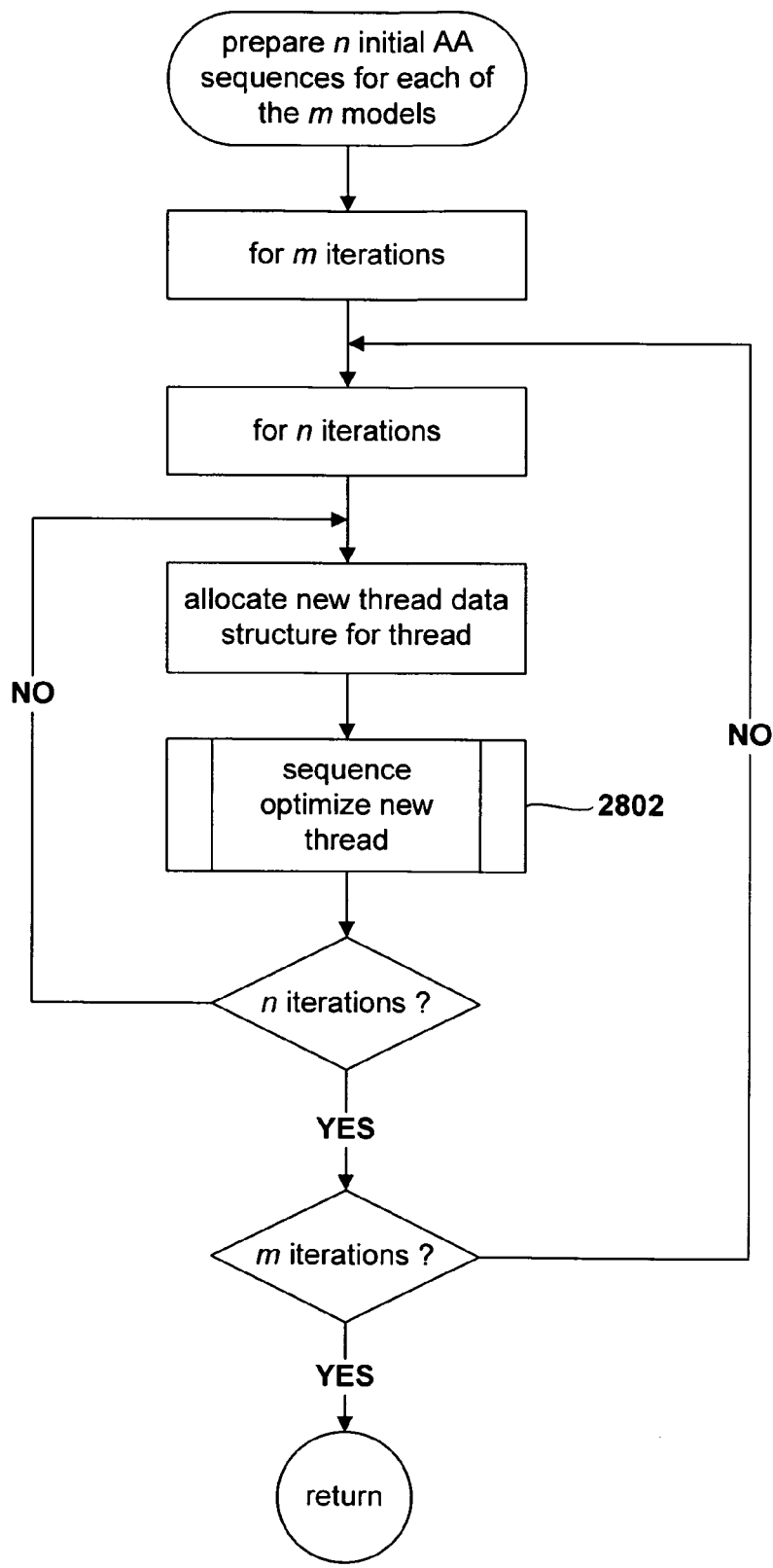
FIG. 28 is a control-flow diagram for the third step (2506 in FIG. 25) of the routine "design protein."

FIG. 28 is a control-flow diagram for the third step (2506 in FIG. 25) of the routine "design protein." FIG. 28 is a control-flow diagram for the third high-level step 2506 in FIG. 25. In this high-level step, the sequences for m threads for each of the m initial models are computed, using a sequence optimization method, in step 2802, described below.

Figure 29:
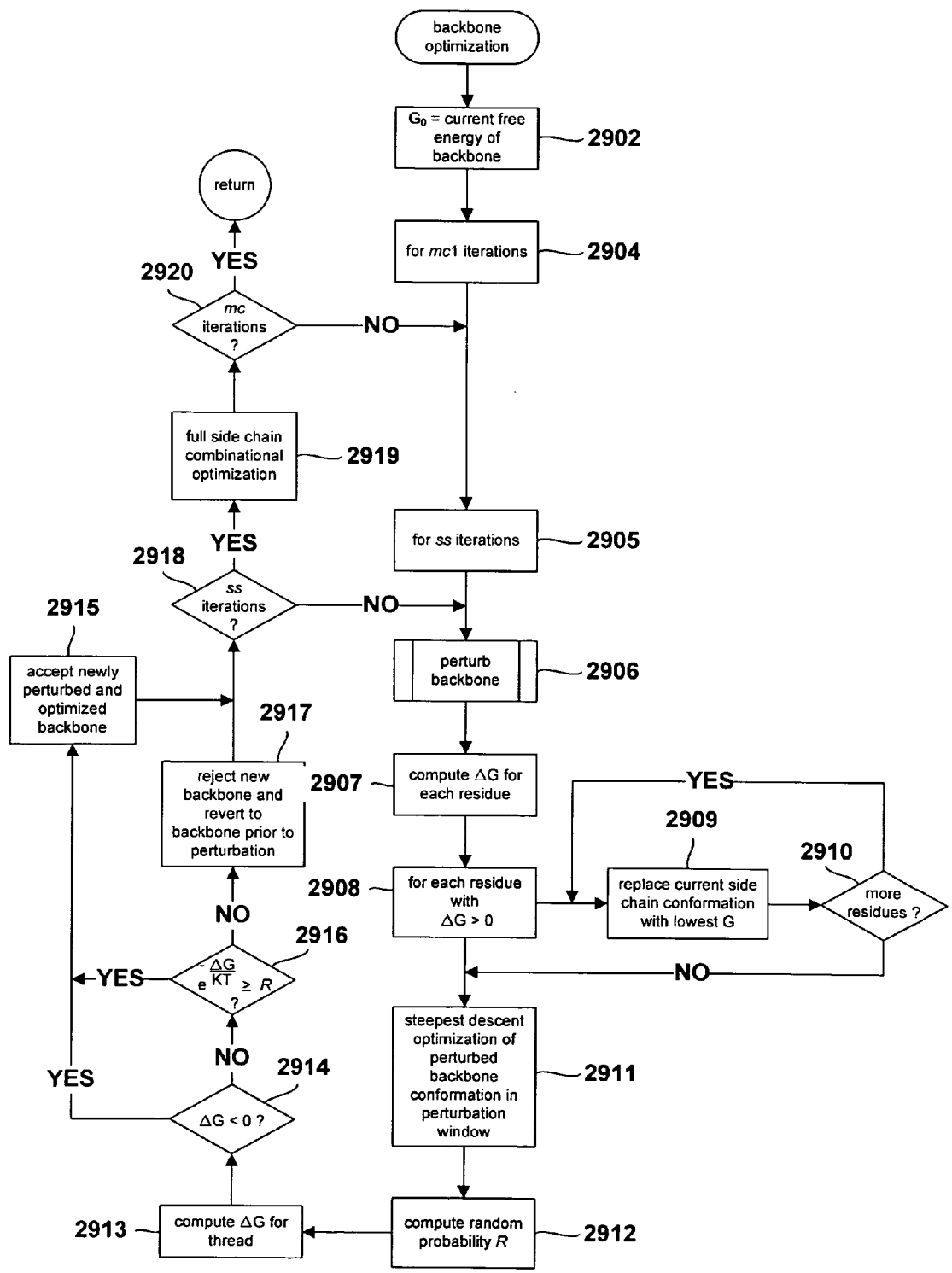
FIG. 29 is a control-flow diagram for the backbone optimization step (2509 in FIG. 25) of the routine "design protein."

FIG. 29 is a control-flow diagram for the backbone optimization step (2509 in FIG. 25) of the routine "design protein." First, in step 2902, the current free energy of the conformation of the current sequence of a thread is noted. In general, this free energy is available from a previous step. In the for-loop of steps 2904-2920, mc1 iterations of Metropolis-Monte-Carlo optimization of the backbone conformation of the current thread are carried out. During these mc1 iterations, ss iterations of the optimization method are carried out in the for-loop of steps 2905-2918, followed by a full backbone and side-chain conformation optimization. In step 2906, the backbone conformation of the thread is perturbed, by a means discussed below, with the current backbone saved in memory prior to the perturbation. Next, in step 2907, the free energy change ΔG for each residue of the thread-sequence is computed. In the for-loop of steps 2908-2910, for each residue with a positive ΔG change, the conformation of the side chain of the residue is optimized with respect to free energy by considering all possible rotamers for the side chain.

A rotomer is a fixed set of side-chain X torsion angles. Rather than continuously modifying X torsion angles in order to optimize side chain conformation, only a discrete set of rotomers, or fixed X torsion angles, are considered for each different type of side chain. Thus, rotomers represent a discretization of the continuous range of possible X angles. The rotamer sets for amino acids are determined from observing conformations of amino acid side changes in determined protein structures.

Then, in step 2911, a steepest-descent optimization of the backbone conformation, or Φ and Ψ torsion angles, of the residues within a neighborhood of the perturbed residues is carried out by a Metropolis-Monte Carlo method. A random probability R is computed in step 2912. Then, a free energy change for the perturbed and then relaxed thread backbone conformation is computed, in step 2913. If the free energy change is less than zero, as determined in step 2914, then the perturbed and relaxed backbone conformation is accepted as a next move, in step 2915. Otherwise, the value $e^{-\Delta G/kT}$ is compared to the computed probability R, in step 2916, and the newly perturbed and relaxed backbone conformation is accepted when $e^{-\Delta G/kT}$ is greater or equal to R. The term $e^{-\Delta G/kT}$ is related to Boltzman-distribution-derived probability. Otherwise, the perturbed and relaxed backbone conformation thread conformation reverts back to the thread conformation prior to the most recent execution of step 2906. Step 2916 represents the instability introduced into the optimization by the Metropolis-Monte-Carlo method. The temperature T is a tunable parameter that allows unfavorable moves with respect to the optimization category, in order to allow a optimization path to ascend and descend shallow free energy ridges on the free-energy surface in order to prevent entrapment by shallow minima. This process continues for (mc1)(ss) iterations, with a full side chain optimization occurring after each ss iteration. In an alternative embodiment, the probability R may be computed after step 2914, to avoid computing R for the case where the free energy change is negative.

Figure 30:
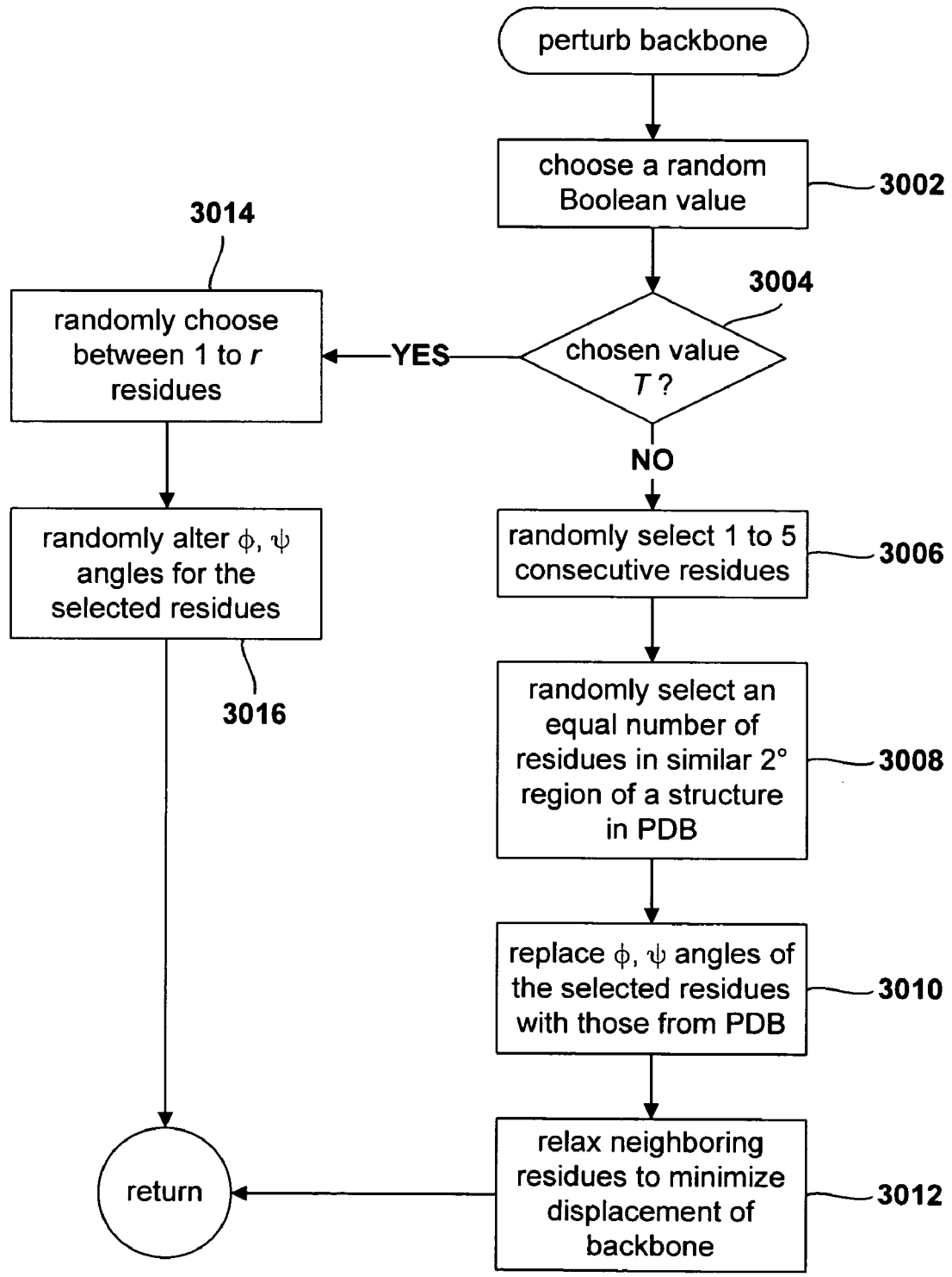
FIG. 30 is a control-flow diagram for the "perturb backbone" step (2906 in FIG. 29) of the backbone optimization routine.

FIG. 30 is a control-flow diagram for the "perturb backbone" step (2906 in FIG. 29) of the backbone optimization routine. First, in step 3002, a random Boolean value is chosen. If the chosen value is FALSE, as determined in step 3004, then steps 3006, 3008, 3010, and 3012 are executed. In these steps, a number between 1 to s of consecutive residues are randomly selected from the thread sequence, where s is a tunable parameter. Then, an equal number of residues in a secondary-structure region equivalent to the secondary-structure region of the selected thread residues, as determined from the initial conformation specification and constraints, are randomly selected from the PBD. The Φ and Ψ angles of the selected thread residues are then replaced with the Φ and Ψ torsion angles of the randomly selected thread resides from the PDB. Finally, the conformations of neighboring residues within a neighborhood surrounding the selected residues are optimized in order to minimize displacement of the backbone due to the perturbation. Alternatively, if the chosen Boolean value is TRUE, as determined in step 3004, then, in step 3014, between 1 and r residues are randomly chosen, where r is a tunable parameter, and the Φ and Ψ torsion angles for the randomly selected residues are slightly and randomly modified in order to perturb the backbone conformation at those selected residues.

Figure 31:
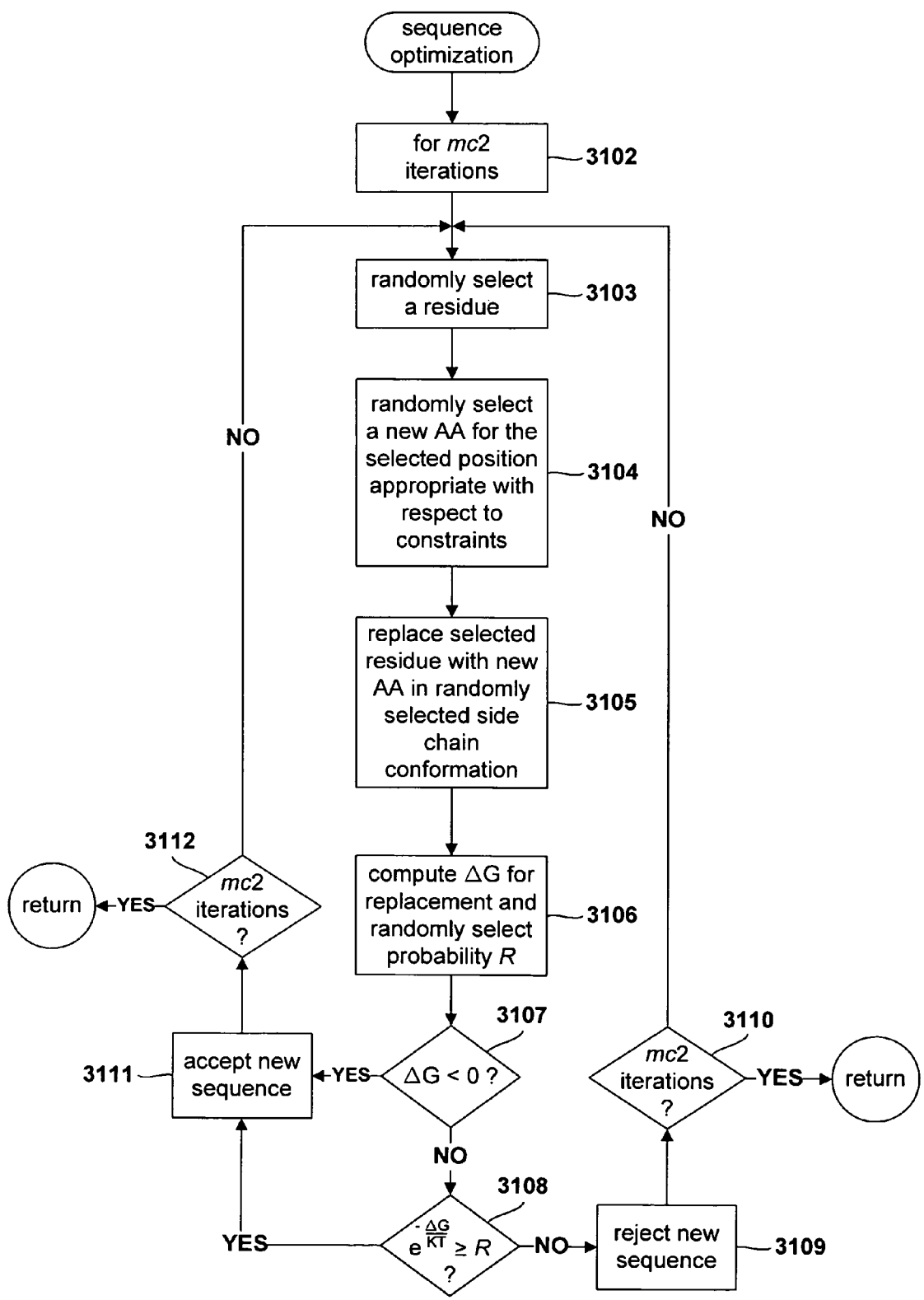
FIG. 31 is a control-flow diagram for the sequence optimization step (2510 of FIG. 25) of the routine "design protein."

FIG. 31 is a control-flow diagram for the sequence optimization step (2510 of FIG. 25) of the routine "design protein." Steps 3102-3112 together compose a for-loop presenting a Metropolis-Monte-Carlo sequence optimization carried out in mc2 iterations, where mc2 is tunable parameter. In a first step, a residue is randomly selected from the thread sequence, in step 3103. Next, in step 3104, a different amino acid is randomly selected to replace the residue selected in step 3103. The randomly selected amino acid is selected to be appropriate for the secondary structure of the residue randomly selected in step 3103, and selected to meet any sequence-related constraints initially specified. The replacement of the newly selected amino acid for the randomly selected amino acid is carried out in step 3105. Next, in step 3106, the free energy change ΔG for the amino-acid-type replacement is computed, and a random probability R is selected. If the ΔG free energy change is less than zero, then the thread sequence incorporating the amino-acid replacement is accepted as a new sequence in step 3111, and the for-loop either continues or terminates, depending on how many iterations of the for-loop have been executed. Otherwise, if the value $e^{-\Delta G/kT}$ is greater or equal to R, as determined in step 3108, then the new sequence is also accepted, in step 3111. Otherwise, the new sequence is rejected, and the thread sequence prior to the replacement step 3105 is retained, in step 3109. Step 3108 represents the instability introduced into the optimization by the Metropolis-Monte-Carlo method. The temperature T is a tunable parameter that allows unfavorable moves with respect to the optimization category, in order to allow a optimization path to ascend and descend shallow free energy ridges on the free-energy surface in order to prevent entrapment by shallow minima. In an alternative embodiment, the probability R may be computed after step 3107, to avoid computing R for the case where the free energy change is negative.

Figure 32:
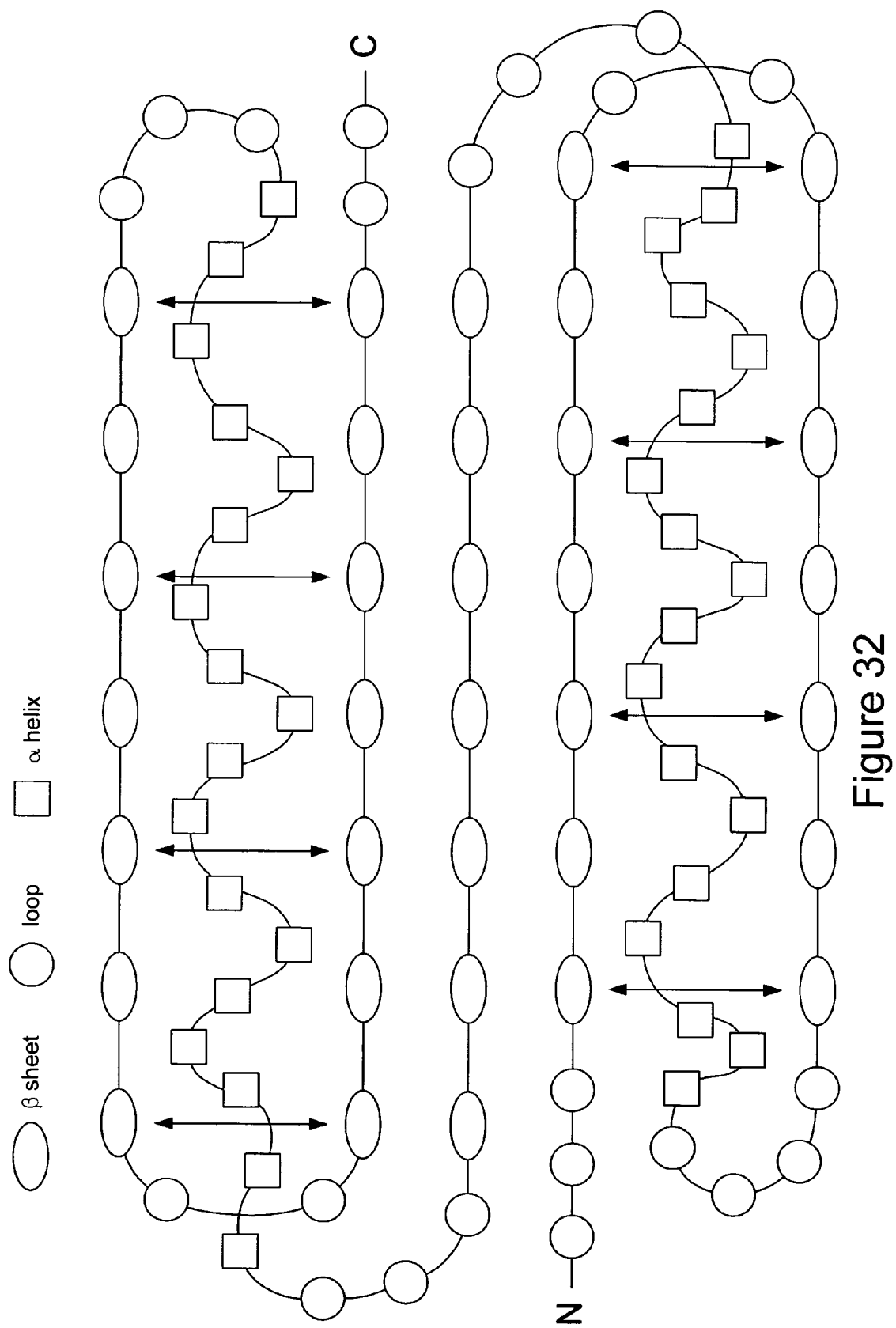
FIG. 32 shows a schematic target conformation and distance constraints used to specify a target polypeptide conformation.
Figure 33:
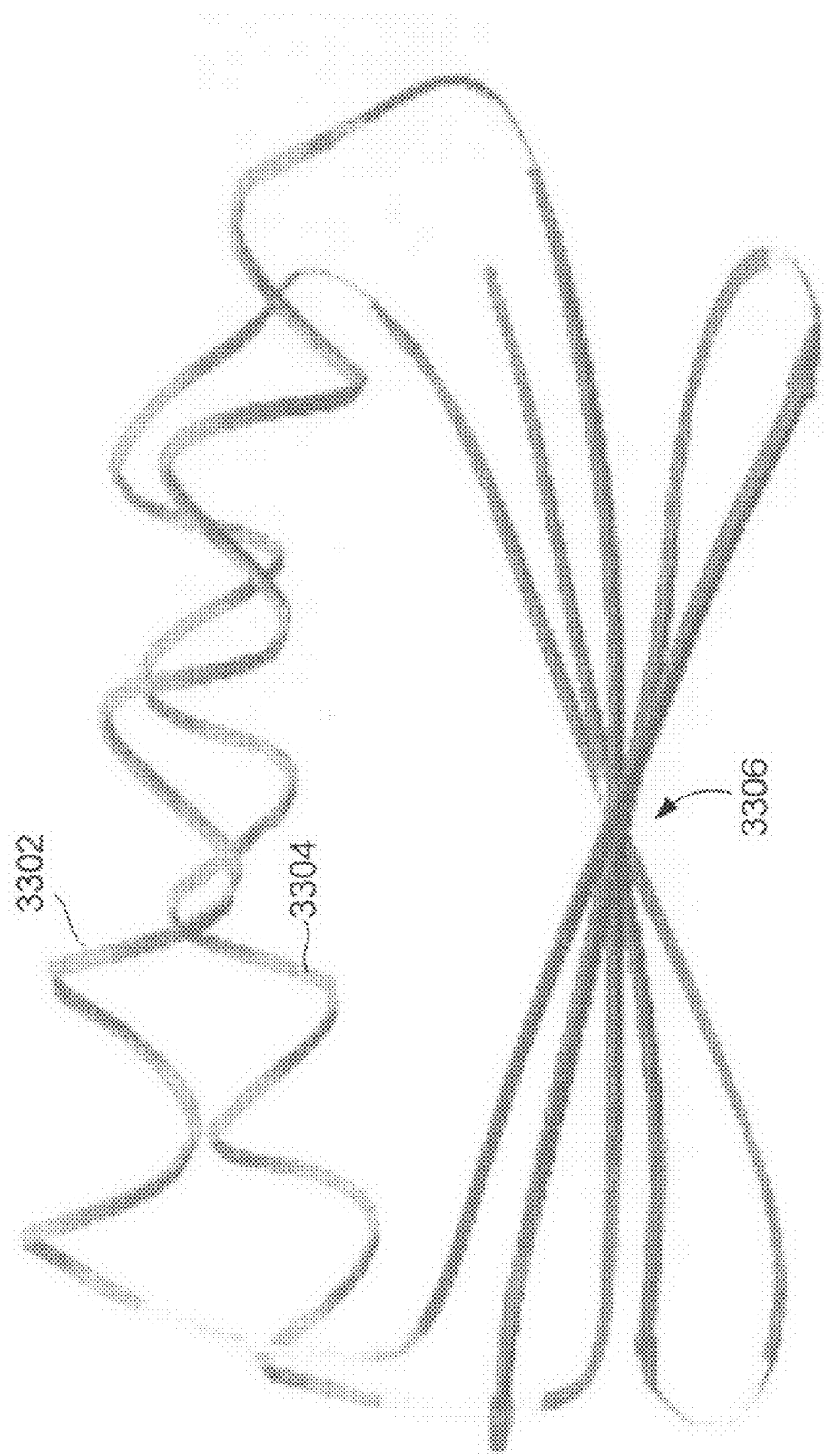
FIG. 33 shows a perspective view of the target conformation shown in FIG. 31.

Specific Amino-Acid Sequence Designed by the Polypeptide-Sequence Design Method That Represents One Embodiment of the Present Invention The polypeptide-sequence design method discussed in the preceding subsection has been successfully used to design a polypeptide having a specified conformation. The polypeptide-sequence design methodology, and the resulting polypeptide sequence and polypeptide-sequence conformation, are described in the article "Design of a Novel Globular Protein Fold With Atomic-Level Accuracy," *Science*, Vol. 302, 21 Nov. 2003, hereby incorporated by reference in its entirety. FIG. 32 shows a schematic target conformation and distance constraints used to specify a target polypeptide conformation. FIG. 33 shows a perspective view of the target conformation shown in FIG. 31. The target conformation includes two α-helical regions 3302 and 3304 overlying a β region 3306. This particular conformation, or protein fold, had not been previously observed in natural proteins. Using the polypeptide-sequence design method discussed in the previous subsection, the following polypeptide-sequence was obtained:

DIQVQVNIDDNGKNFDYTYTVTTE-SELQKVLNELKDYIKKQGAKRVRISITAR TKKEAEK-FAAILIKVFAELGYNDINVTFDGDTVTVEGQLE (SEQ ID NO: 1)

Figure 34:
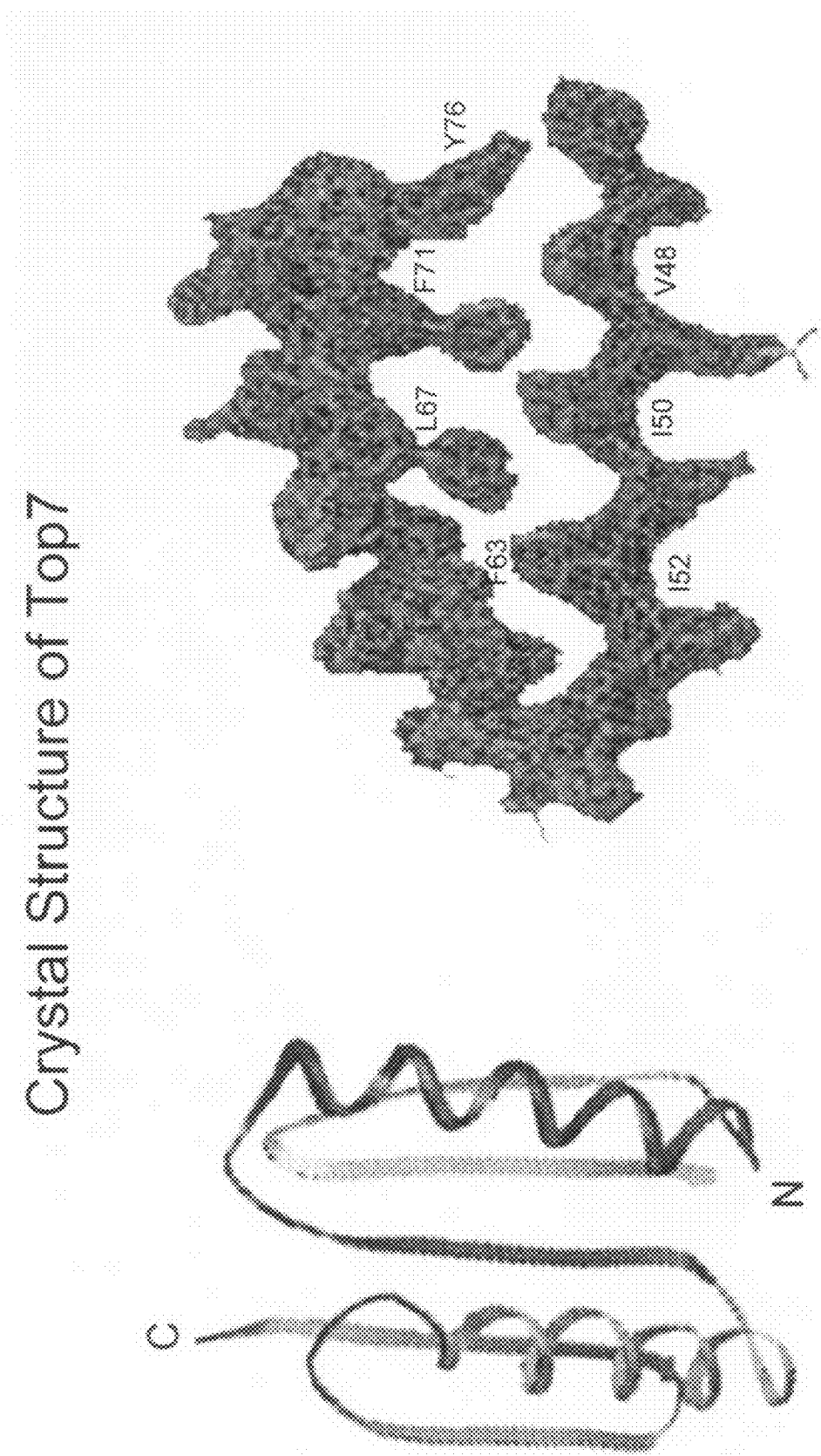
FIG. 34 shows the x-ray structure for top7.
Figure 35:
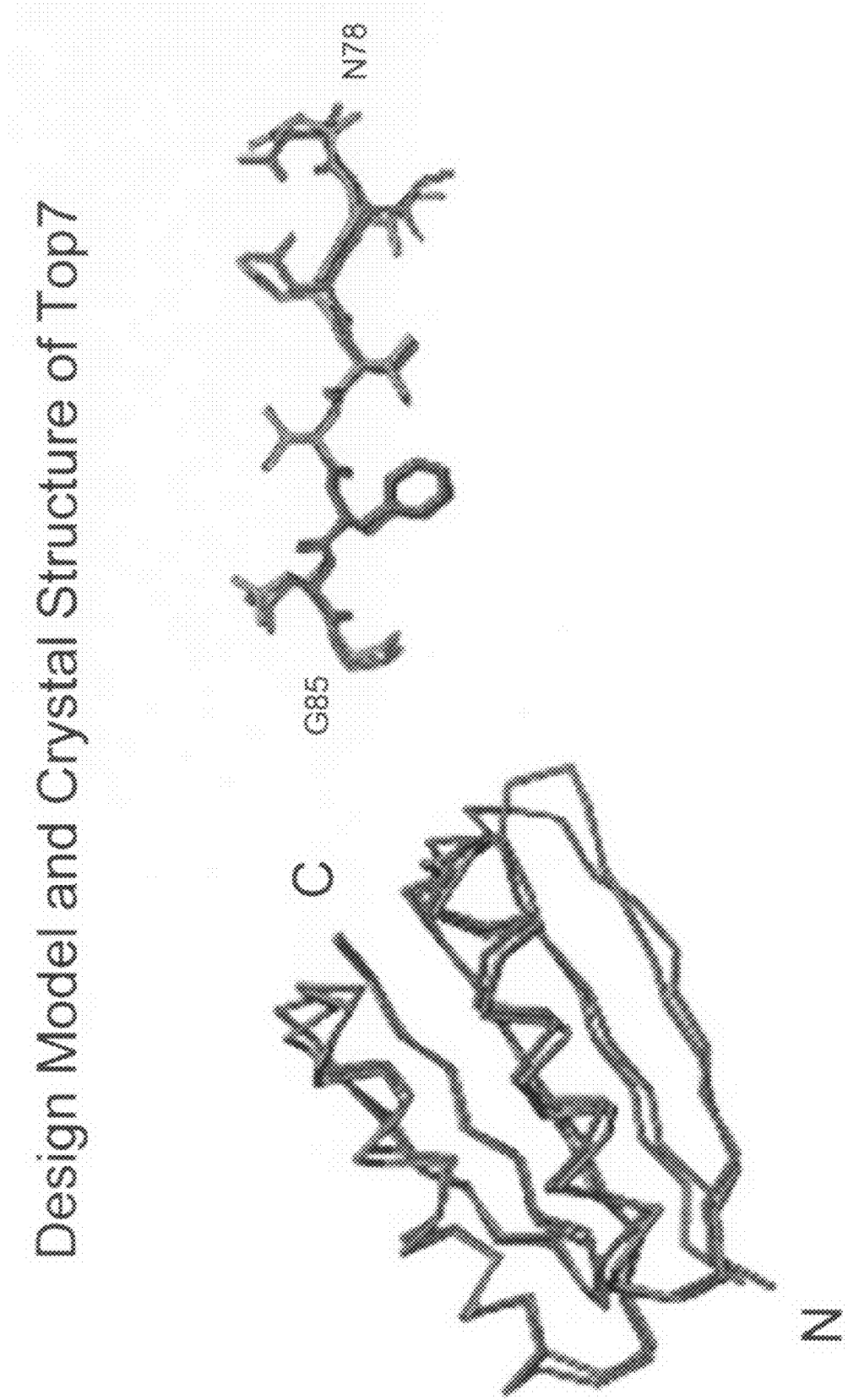
FIG. 35 shows an overlay of a representation of the backbone conformation of the actual synthesized polypeptide, top7, as determined by x-ray crystallography, and the initially specified target conformation.

The polypeptide with this sequence, called "top7," was synthesized, and the resulting polypeptide crystallized for x-ray structure determination. FIG. 34 shows the x-ray structure for top7. Note the strong similarity between the structure shown in FIG. 34 and the target structure shown in FIG. 33. FIG. 35 shows an overlay of a representation of the backbone conformation of the actual synthesized polypeptide, top7, as determined by x-ray crystallography, and the initially specified target conformation. As can be easily determined by visual inspection, the polypeptide-sequence determination method proved to be quite successful in identifying a polypeptide sequence that, instantiated as a synthesized polypeptide, adopts, in solution, the initially specified 3-dimensional conformation.

Although the present invention has been described in terms of a particular embodiment, it is not intended that the invention be limited to this embodiment. Modifications within the spirit of the invention will be apparent to those skilled in the art. For example, an almost limitless number of different software implementations can be designed to carry out the general optimization method discussed in the first subsection, above, and the specific polypeptide-sequence design method discussed in the second subsection. Various implementations can be written in many different programming languages, using different modular organizations, control structures, and varying other such parameters. In addition, a wide variety of alternative methods can be implemented using different local optimization strategies, such as alternatives to the Metropolis-Monte Carlo methods employed in a polypeptide-design method, using different methods for computing state-space trajectories, and different approaches for distributing and parallelizing optimization of individual threads. The polypeptide-sequence design method can be modified to incorporate additional or different types of amino acids, and the polypeptide-sequence-design method can be extended and modified to design other types of biopolymers, potentially including nucleic acids, polysaccharides, and the hybrid biopolymers. Such modifications involve changing the free energy approximation to account for new types of monomers, and the free energy approximation can also be changed to provide correct optimization in different types of chemical environments in which the biopolymer is expected to assume a 3-dimensional conformation. Different free energy approximations may be used in order to compute free energies to direct, or drive, the optimization of polymer sequences in sequence/conformation space, and different optimization criteria may be used, in place of the free energy criterion. The general optimization method discussed in the first subsection has wide applicability to many different high-dimensional optimization problems. Different partitionings of the dimensionality may be employed to facilitate computational efficiency. In descriptions of the general method and in the polypeptide-design method, two partitionings are used, and the high-level iterative optimization alternates between optimization with respect to the dimensions in one partition and optimization with respect to the dimensions in the second partition. In alternative embodiments, greater than two partitionings may be used, with alternating optimizations with respect to each of the greater than two partitions in each high-level iteration step.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

The invention claimed is:

1. A method, carried out on an electronic computer, for determining a monomer sequence for a polymer in order to produce a polymer that adopts a specific, predetermined 3-dimensional conformation in a specified chemical environment, the method comprising:
   receiving, by the electronic computer, a specification of a desired 3-dimensional conformation;
   selecting, by the electronic computer, a number m of initial polymer-backbone conformations, where m is greater than 1;
   for each of the m initial polymer-backbone conformations, selecting, by an electronic computer, a number n of initial sequences, where n is greater than 1, thereby creating mn threads;
   iteratively
      optimizing, by the electronic computer, the polymer-backbone conformations of each thread with respect to an estimated free energy, and
      optimizing, by the electronic computer, the polymer sequence of each thread with respect to an estimated free energy; and
   outputting, by the electronic computer, final monomer sequences of a number of threads to a user by listing each of the number of threads in a computer-readable medium or on a display device, the listing indicating, for each of the number of threads, a probability or relative probability that a polymer having a sequence of the thread adopts the desired 3-dimensional conformation.

2. The method of claim 1 wherein the specification of a desired 3-dimensional conformation includes one or more of:
   a polymer-backbone length, in monomers;
   a polymer-backbone shape;
   sequence constraints;
   distance-between-specific-monomer constraints; and
   local conformation constraints.

3. The method of claim 1 wherein selecting a number m of initial polymer-backbone conformations further comprises:
   for the m of initial polymer-backbone conformations,
      initializing a currently considered initial-polymer-backbone-conformation data structure; and
      iteratively
         selecting a polymer-subsequence-backbone conformation from a known polymer compatible with the specification of a desired 3-dimensional conformation; and
         adding the selected polymer-subsequence-backbone conformation to the currently considered initial-polymer-backbone-conformation data structure
         until a complete initial polymer-backbone conformation has been constructed in the initial-polymer-backbone-conformation data structure.

4. The method of claim 1 wherein selecting a number n of initial sequences for a thread further comprises;
   allocating a number n of thread data structures, each thread data structure initialized to have a selected polymer-backbone conformation; and
   for each thread data structure,
      iteratively
         randomly selecting a monomer position within the thread data structure and randomly assigning a particular type of monomer and monomer conformation for the position; and
         evaluating a free energy for a polymer described by the resulting thread data structure to either accept the randomly assigned monomer type at the randomly selected monomer position or to reject the randomly assigned monomer type at the randomly selected monomer position.

5. The method of claim 1 wherein optimizing a polymer-backbone conformation of a thread further comprises:
   iteratively,
      locally and randomly perturbing a current polymer-backbone conformation of the thread;
      relaxing the polymer-backbone conformation with respect to the perturbation; and
      evaluating a free energy for a polymer described by the resulting thread to either accept the locally and randomly perturbed conformation or to reject the locally and randomly perturbed conformation.

6. The method of claim 5 wherein evaluating a free energy for a polymer described by the resulting thread to either accept the locally and randomly perturbed conformation or to reject the locally and randomly perturbed conformation further comprises:
   when the evaluated free energy for the polymer described by the resulting thread is lower than a free energy computed for the thread prior to the perturbation, accepting the locally and randomly perturbed conformation;
   when a probability proportional to $e^{-\Delta/T}$, where $\Delta$ is a difference between the evaluated free energy for the polymer described by the resulting thread and the free energy computed for the thread prior to the perturbation and T is a tunable parameter, is greater than or equal to a randomly selected probability, accepting the locally and randomly perturbed conformation; and
   otherwise rejecting the locally and randomly perturbed conformation.

7. The method of claim 1 wherein optimizing the polymer sequence of a thread further includes:
   randomly selecting a monomer position within the thread and randomly assigning a randomly selected monomer type and monomer conformation for the position; and
   evaluating a free energy for a polymer described by the resulting thread to either accept the randomly assigned monomer type at the randomly selected monomer position or to reject the randomly assigned monomer type at the randomly selected monomer position.

8. The method of claim 7 wherein evaluating a free energy for a polymer described by the resulting thread to either accept the randomly assigned monomer type at the randomly selected monomer position or to reject the randomly assigned monomer type at the randomly selected monomer position further comprises:
   when the evaluated free energy for the polymer described by the resulting thread is lower than a free energy computed for the polymer described by the thread prior to randomly selecting the monomer position within the thread and randomly assigning the randomly selected monomer type and monomer conformation for the position, accepting the randomly assigned monomer type and conformation at the randomly selected position;

when a probability proportional to $e^{-\Delta/T}$, where $\Delta$ is a difference between the evaluated free energy for the polymer described by the resulting thread and the free energy computed for the thread prior to prior to randomly selecting the monomer position within the thread and randomly assigning the randomly selected monomer type and monomer conformation for the position, is greater than or equal to a randomly selected probability, accepting the randomly assigned monomer type and conformation at the randomly selected position; and otherwise rejecting the accepting the randomly assigned monomer type and conformation at the randomly selected position.

9. The method of claim 8 wherein outputting final monomer sequences of each thread to a user by listing the threads in a computer-readable medium or on a display device in order of a probability that a polymer having a sequence of the thread adopts the desired 3-dimensional conformation further comprises:

outputting final monomer sequences of each thread to a user by listing the threads in a computer-readable medium or on a display device in increasing order of free energy calculated for a polymer described by the thread.

10. The method of claim 1 wherein the polymer is a polypeptide;

wherein monomers are amino acids; and wherein polypeptide-backbone conformations and amino-acid sequences of a thread are optimized with respect to free energy of a polymer described by the thread in solution, the free energy approximated by free energy terms related to amino acids and free energy terms related to pair-wise interaction of amino-acids.

11. Computer instruction encoded in a computer-readable medium that implement a method, carried out on an electronic computer, for determining a monomer sequence for a polymer in order to produce a polymer that adopts a specific, predetermined 3-dimensional conformation in a specified chemical environment by:

receiving, by the electronic computer, a specification of a desired 3-dimensional conformation;

selecting, by the electronic computer, a number m of initial polymer-backbone conformations, where m is greater than 1;

for each of the m initial polymer-backbone conformations, selecting, by the electronic computer, a number n of initial sequences, where n is greater than 1, thereby creating mn threads;

iteratively optimizing, by the electronic computer, the polymer-backbone conformations of each thread with respect to an estimated free energy, and optimizing, by the electronic computer, the polymer sequence of each thread with respect to an estimated free energy; and outputting, by the electronic computer, final monomer sequences of a number of threads to a user by listing each of the number of threads in a computer-readable medium or on a display device, the listing indicating, for each of the number of threads, a probability or relative probability that a polymer having a sequence of the thread adopts the desired 3-dimensional conformation.

12. A computer system comprising:

one or more processors; and a program running on the one or more processors that determines a monomer sequence for a polymer in order to produce a polymer that adopts a specific, predetermined 3-dimensional conformation in a specified chemical environment by:

receiving, by the electronic computer, a specification of a desired 3-dimensional conformation;

selecting, by the electronic computer, a number m of initial polymer-backbone conformations, where m is greater than 1;

for each of the m initial polymer-backbone conformations, selecting, by the electronic computer, a number n of initial sequences, where n is greater than 1, thereby creating mn threads;

iteratively optimizing, by the electronic computer, the polymer-backbone conformations of each thread with respect to an estimated free energy, and optimizing, by the electronic computer, the polymer sequence of each thread with respect to an estimated free energy; and outputting, by the electronic computer, final monomer sequences of a number of threads to a user by listing each of the number of threads in a computer-readable medium or on a display device, the listing indicating, for each of the number of threads, a probability or relative probability that a polymer having a sequence of the thread adopts the desired 3-dimensional conformation.

13. The computer of claim 12 wherein the specification of a desired 3-dimensional conformation includes one or more of:

a polymer-backbone length, in monomers;

a polymer-backbone shape;

sequence constraints;

distance-between-specific-monomer constraints; and local conformation constraints.

14. The computer of claim 12 wherein the computer selects a number m of initial polymer-backbone conformations further by:

for the m of initial polymer-backbone conformations, initializing a currently considered initial-polymer-backbone-conformation data structure; and iteratively selecting a polymer-subsequence-backbone conformation from a known polymer compatible with the specification of a desired 3-dimensional conformation; and adding the selected polymer-subsequence-backbone conformation to the currently considered initial-polymer-backbone-conformation data structure until a complete initial polymer-backbone conformation has been constructed in the initial-polymer-backbone-conformation data structure.

15. The computer of claim 12 wherein the computer selects a number n of initial sequences for a thread by;

allocating a number n of thread data structures, each thread data structure initialized to have a selected polymer-backbone conformation; and for each thread data structure, iteratively randomly selecting a monomer position within the thread data structure and randomly assigning a particular type of monomer and monomer conformation for the position; and evaluating a free energy for a polymer described by the resulting thread data structure to either accept the randomly assigned monomer type at the randomly selected monomer position or to reject the randomly assigned monomer type at the randomly selected monomer position.

16. The computer of claim 12 wherein the computer optimizes a polymer-backbone conformation of a thread by:
iteratively,
locally and randomly perturbing a current polymer-backbone conformation of the thread;
relaxing the polymer-backbone conformation with respect to the perturbation; and
evaluating a free energy for a polymer described by the resulting thread to either accept the locally and randomly perturbed conformation or to reject the locally and randomly perturbed conformation.

17. The computer of claim 16 wherein the computer evaluates a free energy for a polymer described by the resulting thread to either accept the locally and randomly perturbed conformation or to reject the locally and randomly perturbed conformation by:
when the evaluated free energy for the polymer described by the resulting thread is lower than a free energy computed for the thread prior to the perturbation, accepting the locally and randomly perturbed conformation;
when a probability proportional to $e^{-\Delta/T}$, where $\Delta$ is a difference between the evaluated free energy for the polymer described by the resulting thread and the free energy computed for the thread prior to the perturbation and T is a tunable parameter, is greater than or equal to a randomly selected probability, accepting the locally and randomly perturbed conformation; and
otherwise rejecting the locally and randomly perturbed conformation.

18. The computer of claim 12 wherein the computer optimizes the polymer sequence of a thread by:
randomly selecting a monomer position within the thread and randomly assigning a randomly selected monomer type and monomer conformation for the position; and
evaluating a free energy for a polymer described by the resulting thread to either accept the randomly assigned monomer type at the randomly selected monomer position or to reject the randomly assigned monomer type at the randomly selected monomer position.

19. The computer of claim 18 wherein the computer evaluates a free energy for a polymer described by the resulting thread to either accept the randomly assigned monomer type at the randomly selected monomer position or to reject the randomly assigned monomer type at the randomly selected monomer position by:
when the evaluated free energy for the polymer described by the resulting thread is lower than a free energy computed for the polymer described by the thread prior to randomly selecting the monomer position within the thread and randomly assigning the randomly selected monomer type and monomer conformation for the position, accepting the randomly assigned monomer type and conformation at the randomly selected position;
when a probability proportional to $e^{-\Delta/T}$, where $\Delta$ is a difference between the evaluated free energy for the polymer described by the resulting thread and the free energy computed for the thread prior to prior to randomly selecting the monomer position within the thread and randomly assigning the randomly selected monomer type and monomer conformation for the position, is greater than or equal to a randomly selected probability, accepting the randomly assigned monomer type and conformation at the randomly selected position; and
otherwise rejecting the accepting the randomly assigned monomer type and conformation at the randomly selected position.

20. The computer system of claim 12
wherein the polymer is a polypeptide;
wherein monomers are amino acids; and
wherein polypeptide-backbone conformations and amino-acid sequences of a thread are optimized with respect to free energy of a polymer described by the thread in solution, the free energy approximated by free energy terms related to amino acids and free energy terms related to pair-wise interaction of amino-acids.

* * * * *